United States Patent
Kassab et al.

(10) Patent No.: US 11,090,180 B2
(45) Date of Patent: Aug. 17, 2021

(54) INTESTINAL DEVICES AND METHODS FOR FACILITATING WEIGHT LOSS

(71) Applicant: 3DT Holdings, LLC, San Diego, CA (US)

(72) Inventors: Ghassan S. Kassab, La Jolla, CA (US); Xiao Lu, San Diego, CA (US)

(73) Assignee: 3DT Holdings, LLC, San Diego, CA (US)

( * ) Notice: Subject to any disclaimer, the term of this patent is extended or adjusted under 35 U.S.C. 154(b) by 710 days.

(21) Appl. No.: 15/819,657

(22) Filed: Nov. 21, 2017

(65) Prior Publication Data

US 2018/0200095 A1 Jul. 19, 2018

Related U.S. Application Data

(63) Continuation of application No. 14/368,988, filed as application No. PCT/US2012/071560 on Dec. 23, 2012, now Pat. No. 9,820,879.

(60) Provisional application No. 61/580,293, filed on Dec. 26, 2011.

(51) Int. Cl.
  *A61F 5/00* (2006.01)
(52) U.S. Cl.
  CPC ............ *A61F 5/0076* (2013.01); *A61F 5/005* (2013.01); *A61F 5/0079* (2013.01)
(58) Field of Classification Search
  CPC ........................................... A61F 5/005–0079
  See application file for complete search history.

(56) References Cited

U.S. PATENT DOCUMENTS

| | | | |
|---|---|---|---|
| 4,403,604 A | 9/1983 | Wilkinson et al. | |
| 6,572,627 B2 * | 6/2003 | Gabbay | A61F 5/0063 606/151 |
| 6,676,674 B1 * | 1/2004 | Dudai | A61B 17/12 606/151 |
| 2004/0230137 A1 * | 11/2004 | Mouton | A61F 5/0083 600/593 |
| 2005/0038458 A1 * | 2/2005 | Bailly | A61F 5/0066 606/157 |
| 2005/0119674 A1 * | 6/2005 | Gingras | A61F 5/0086 606/151 |
| 2007/0265646 A1 * | 11/2007 | McCoy | A61F 5/0079 606/157 |

(Continued)

FOREIGN PATENT DOCUMENTS

| | | | |
|---|---|---|---|
| WO | 2008/109527 A2 | 9/2008 | |
| WO | WO-2008147582 A2 * | 12/2008 | ........... A61F 5/0086 |
| WO | 2010/085649 A1 | 7/2010 | |

OTHER PUBLICATIONS

International Searching Authority, International Search Report, dated Mar. 8, 2013, PCT/US2012/071560.

(Continued)

*Primary Examiner* — Benjamin J Klein
(74) *Attorney, Agent, or Firm* — Reichel Stohry Dean LLP; Mark C. Reichel; Natalie J. Dean

(57) ABSTRACT

Intestinal devices and methods for facilitating weight loss. In at least one embodiment of a method of patient treatment of the present disclosure, the method comprises the step of positioning a device, that is configured to reduce or limit localized intestinal distension, around a portion of an intestine of a patient.

20 Claims, 11 Drawing Sheets

(56) References Cited

U.S. PATENT DOCUMENTS

| | | | | |
|---|---|---|---|---|
| 2008/0319435 | A1* | 12/2008 | Rioux | A61F 5/005 606/33 |
| 2009/0216254 | A1* | 8/2009 | Harris | A61B 17/1114 606/153 |
| 2010/0145324 | A1* | 6/2010 | Nihalani | A61F 5/0063 606/14 |
| 2010/0298632 | A1 | 11/2010 | Levine et al. | |
| 2011/0009690 | A1* | 1/2011 | Belhe | A61F 5/0076 600/37 |
| 2011/0066254 | A1 | 3/2011 | Forsell et al. | |
| 2011/0270018 | A1 | 11/2011 | Honaryar et al. | |
| 2013/0331642 | A1* | 12/2013 | Schauer | A61F 5/0076 600/37 |

OTHER PUBLICATIONS

International Searching Authority, Written Opinion of the International Searching Authority, dated Mar. 8, 2013, PCT/US2012/071560.

European Search Opinion and Supplemental European Search Report, EP 12862624.9, dated Nov. 19, 2014.

* cited by examiner

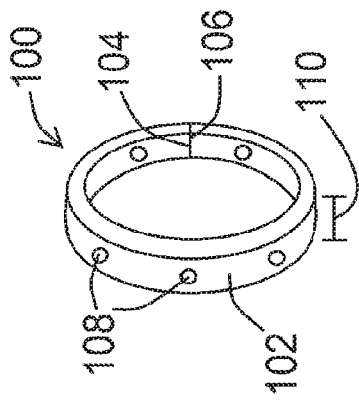
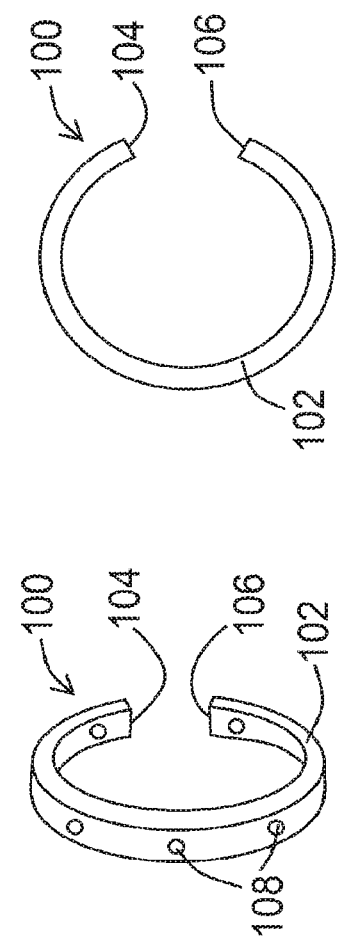
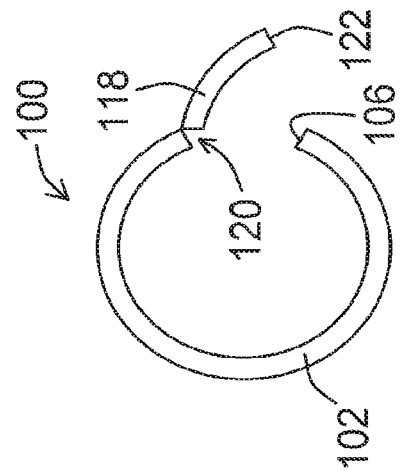
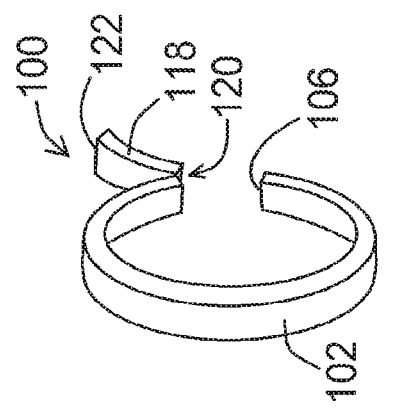
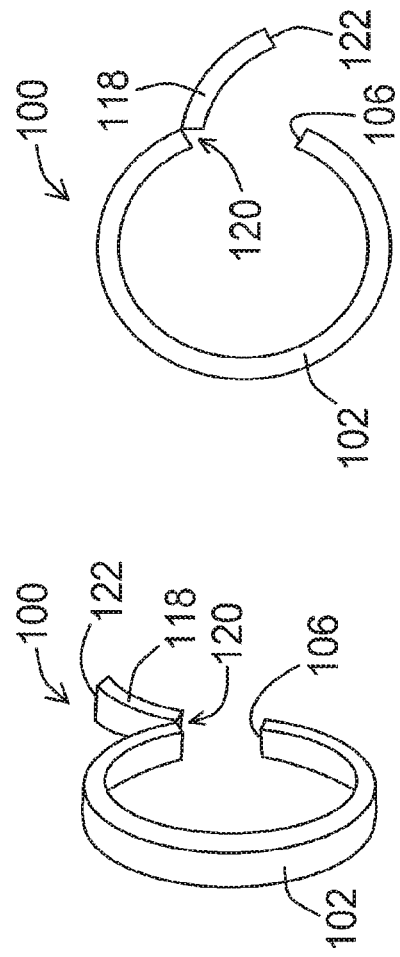
FIG. 1A  FIG. 1B  FIG. 1C  FIG. 1D  FIG. 1E  FIG. 1F

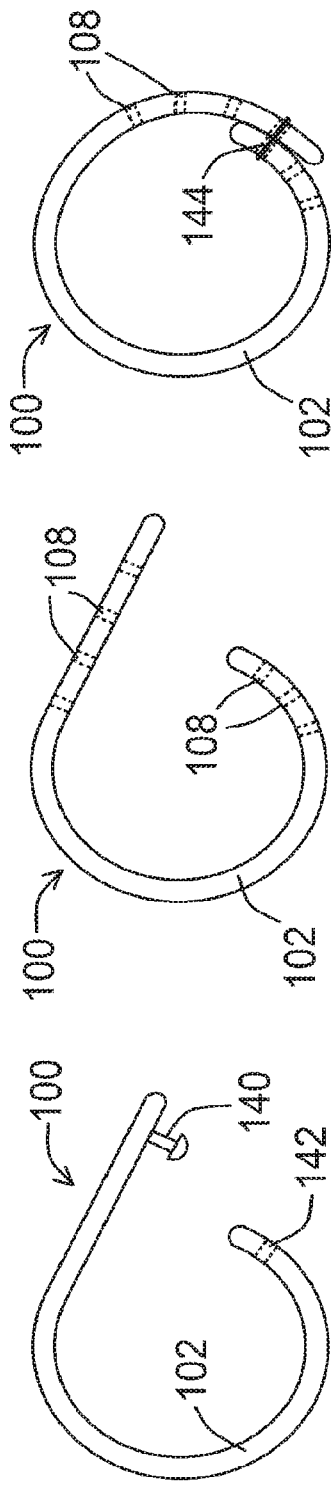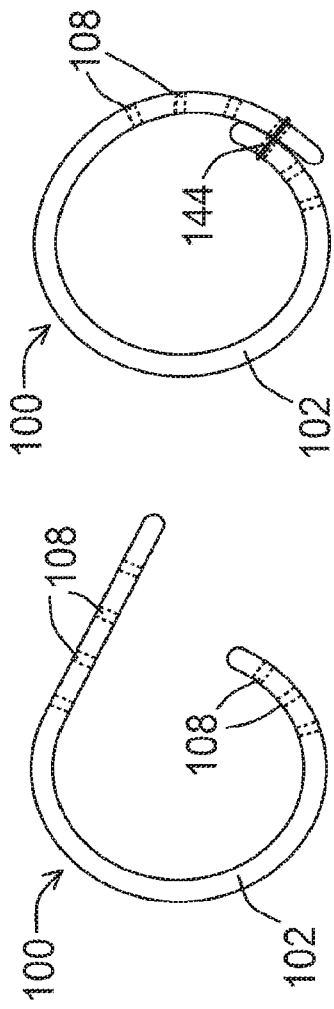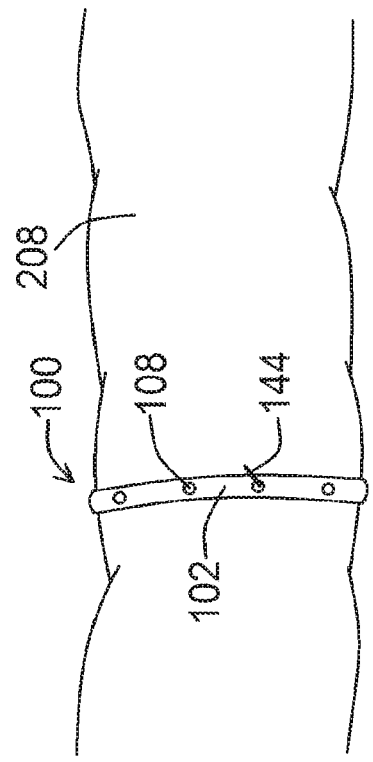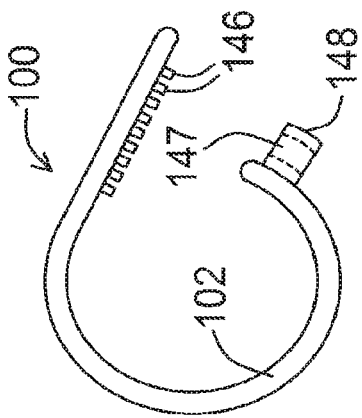

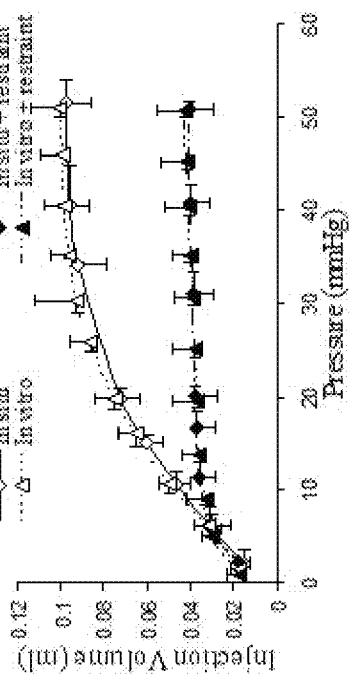
FIG. 3A: Duodenum
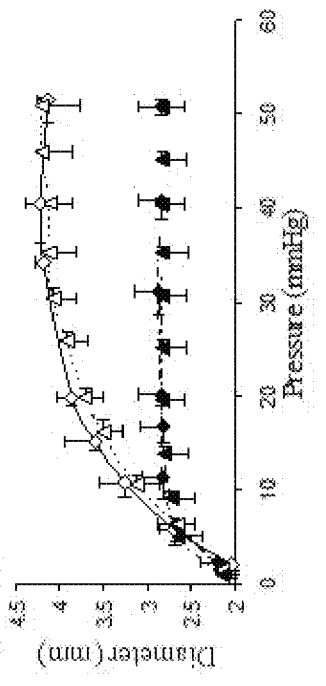
FIG. 3C: Duodenum
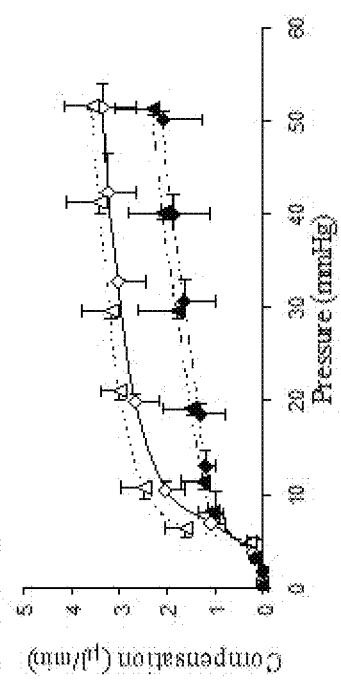
FIG. 3E: Duodenum
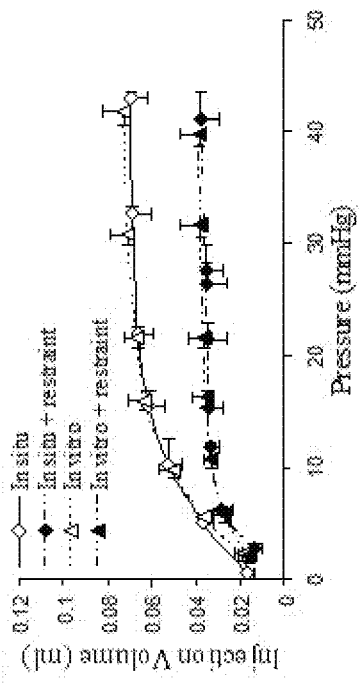
FIG. 3B: Colon
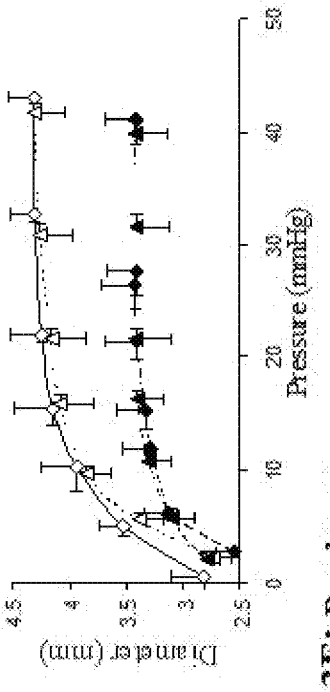
FIG. 3D: Colon
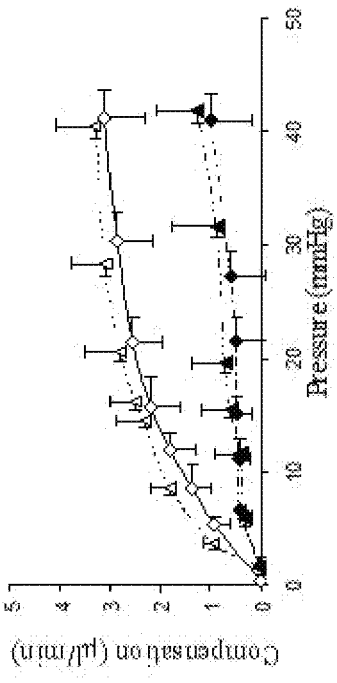
FIG. 3F: Colon

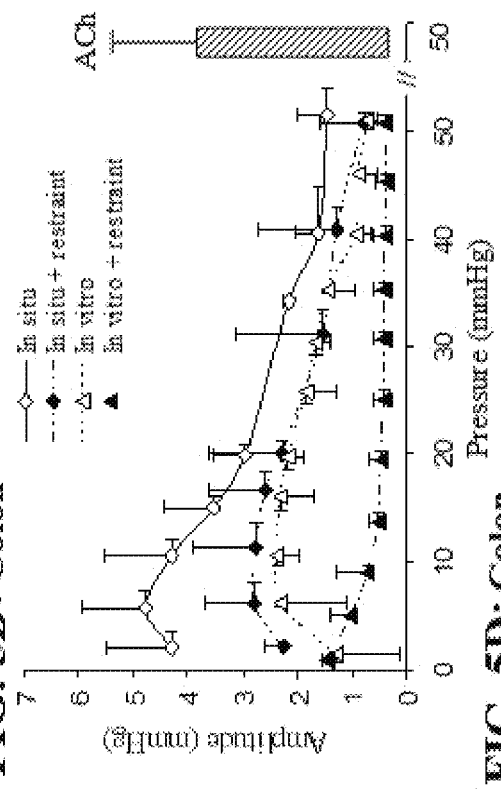
FIG. 5A: Duodenum
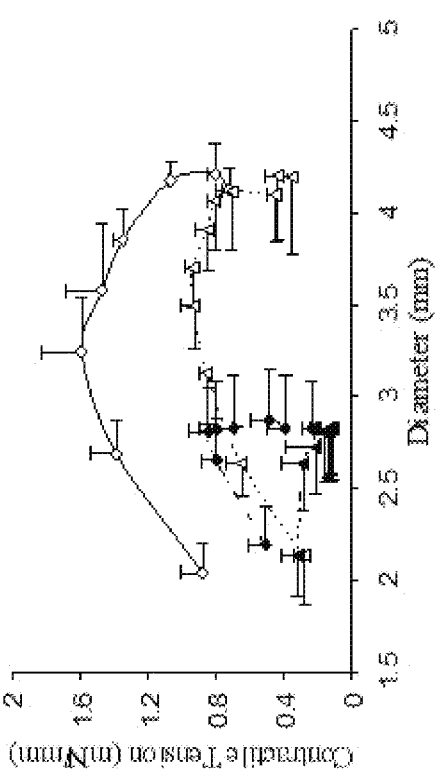
FIG. 5C: Duodenum
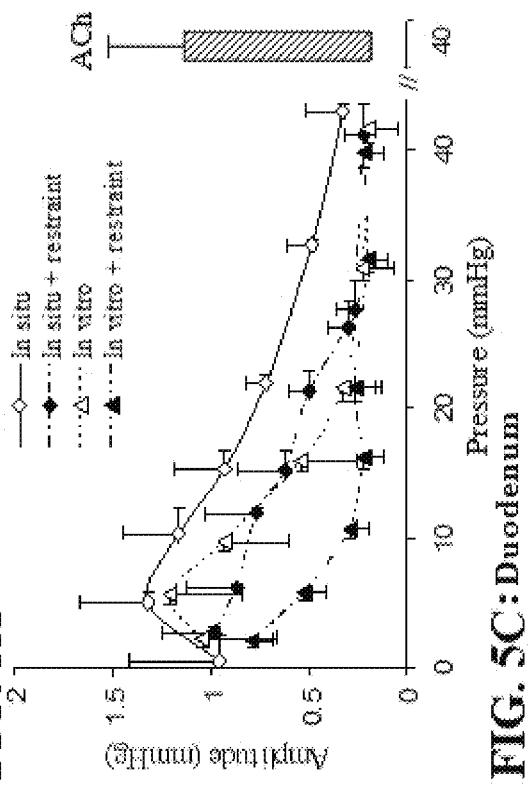
FIG. 5B: Colon
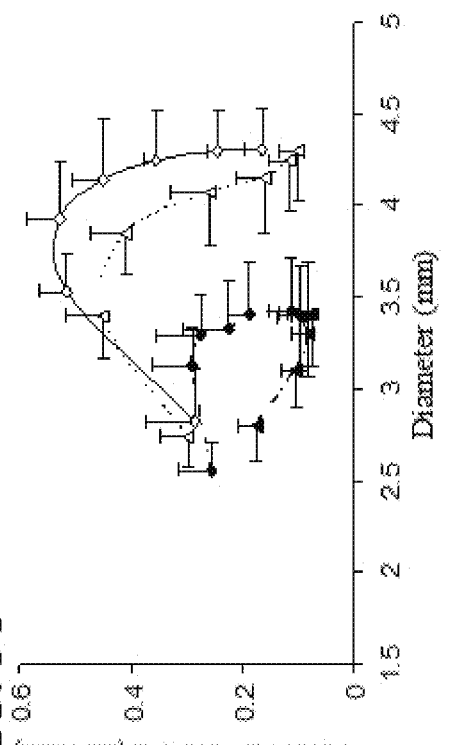
FIG. 5D: Colon

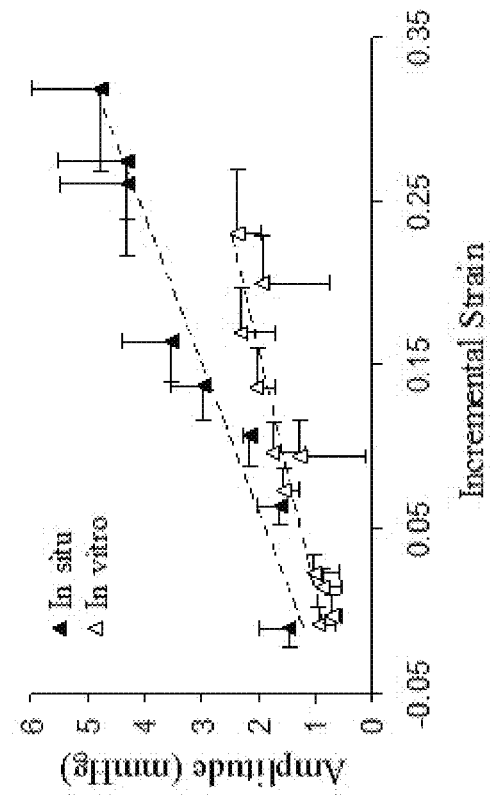
FIG. 6A: Duodenum
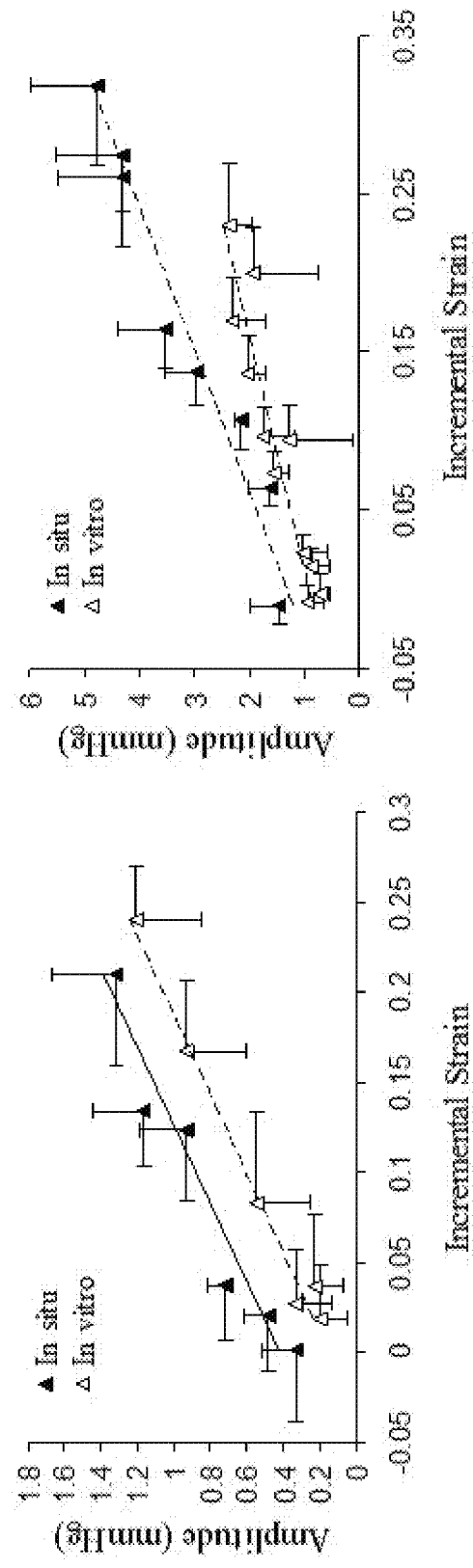
FIG. 6B: Colon
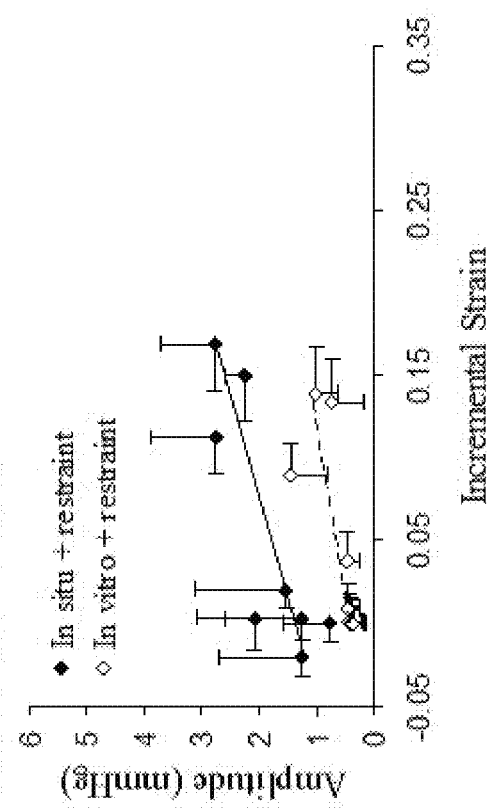
FIG. 6C: Duodenum
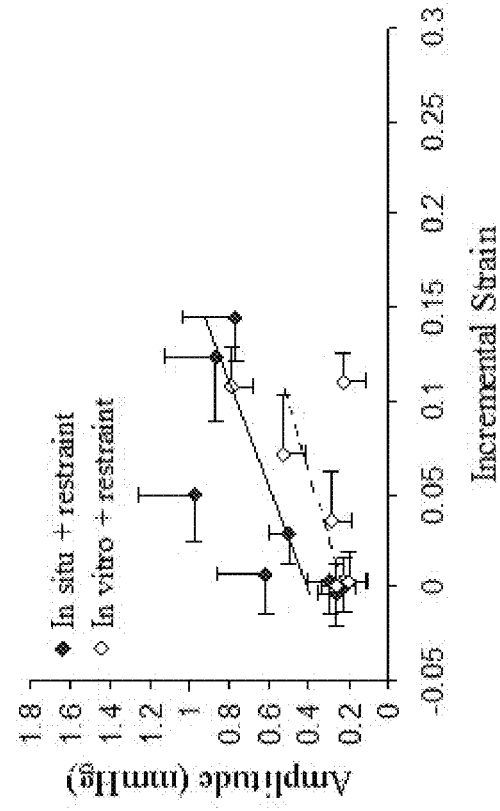
FIG. 6D: Colon

INTESTINAL DEVICES AND METHODS FOR FACILITATING WEIGHT LOSS

PRIORITY

The present application is related to, claims the priority benefit of, and is a U.S. continuation application of, U.S. patent application Ser. No. 14/368,988, filed Jun. 26, 2014 and issued as U.S. Pat. No. 9,820,879 on Nov. 21, 2017, which is related to, claims the priority benefit of, and is a U.S. § 371 National Stage Application of, PCT Patent Application Serial No. PCT/US2012/071560, filed Dec. 23, 2012, which is related to, and claims the priority benefit of, U.S. Provisional Patent Application Ser. No. 61/580,293 filed Dec. 26, 2011. The contents of each of the aforementioned patent applications are hereby incorporated by reference in their entirety into this disclosure.

BACKGROUND

Physical forces act on the intestinal wall when the intestine propels chime. The intestinal tract is abundantly innervated with mechanosensors to sense the physical forces in intestinal wall when a meal transits through the gut. The excitation of extrinsic sensory afferents provides clear evidence of the intestinal mechanosensory endings in response to distension. These sensory afferents respond to mechanical stimulation arising during intestinal distension and contraction. The level of mesenteric afferent firing increases in proportion to the increase in intraintestinal pressure.

Brain-gut interactions are recognized as major players in physiological and pathpophysiological regulation of the intestinal tract. The intestinal tract is dominated by enteric nervous system together with the myogenic pacemakers known as interstitial cells of Cajal that allows the intestine to have a considerable degree of independent control from the central nervous system.

Although the mechanical sensory and afferent excitations in response to mechanical stimulation have been extensively studied, the role of mechanical stimulation on intestinal contractility is poorly understood. Intestinal contractility consists of intricate interplay between intestinal sensors to afferent nerves to central nervous system and back to efferent nerves and intestinal smooth muscles.

Unfortunately, there is currently no quantitative method to study the intact (in vitro or in situ) intestinal contractility. To understand the relation between distension (intestinal sensors) and contractility (intestinal smooth muscles), a novel quantitative assay was used, namely an in situ and in vitro isovolumic myograph, to determine the role of extrinsic nervous system and intrinsic nervous regulation on the contractility. An external restraint was used to inhibit the distension and hence determine the role of distension or stretch. Depending on the outcomes of the study, use of such a restraint may be useful to, depending on configuration and placement, operate as a safe and effective weight loss device.

In view of the foregoing, a novel intestinal device and method for using the same to facilitate weight loss, for example, would be well accepted in the marketplace.

BRIEF SUMMARY

In an exemplary method of patient treatment of the present disclosure, the method comprises the step of positioning a device that is configured to reduce or limit localized intestinal distension, around a portion of an intestine of a patient. In another exemplary method of patient treatment of the present disclosure, the method comprises the step of positioning a device around a portion of an intestine of a patient. In another embodiment, the method is performed to facilitate weight loss of the patient. In yet another embodiment, the method is performed to facilitate a reduction in food intake by the patient. In an additional embodiment, the method is performed to treat obesity.

In an exemplary method of patient treatment of the present disclosure, the method is performed to treat a diabetic condition of the patient. In an additional embodiment, the positioning step is performed to reduce or limit localized distension of the intestine, slowing overall digestive and/or excretory processes of the patient. In yet an additional embodiment, the positioning step is performed to facilitate satiety of the patient. In another embodiment, the positioning step is performed to slow overall digestive and/or excretory processes of the patient.

In an exemplary method of patient treatment of the present disclosure, the method further comprises the step of introducing the device into the patient prior to the step of positioning the device. In another embodiment, the introducing step is performed using a procedure selected from the group consisting of a laparoscopic procedure and an open surgical procedure. In yet another embodiment, the method further comprises the step of securing the device to the patient using one or more sutures. In an additional embodiment, the method is performed to treat a blood glucose level condition of the patient.

In an exemplary method of patient treatment of the present disclosure, the positioning step is performed to position the device around at least half of a perimeter of the intestine. In another embodiment, the positioning step is performed to position the device around at least three quarters of a perimeter of the intestine. In yet another embodiment, the positioning step is performed to position the device completely around the intestine. In an additional embodiment, the weight loss of the patient is facilitated by the patient eating less food. In yet an additional embodiment, the weight loss of the patient is facilitated by the patient eating less food due to slower overall digesting and/or excretory processes of the patient.

In an exemplary method of patient treatment of the present disclosure, the device remains within the patient for a desired amount of time. In an additional embodiment, the desired amount of time is selected from the group consisting of at least two weeks, between two weeks and one month, between one month and three months, between three months and six months, between six months and one year, between one year and two years, and at least two years. In yet an additional embodiment, the method further comprises the step of removing the device from the patient after the desired amount of time has elapsed. In another embodiment, the positioning step is performed to position the device around a portion of the intestine at a first location. In yet another embodiment, the method further comprises the step of positioning a second device configured to reduce or limit localized intestinal distension around a portion of the intestine at a second location.

In an exemplary method of patient treatment of the present disclosure, the device is positioned adjacent to the second device. In another embodiment, the device touches the second device. In yet another embodiment, the second device overlaps at least a portion of the device. In an additional embodiment, the device does not touch the second device.

In an exemplary method of patient treatment of the present disclosure, the method further comprises the step of positioning a third device configured to reduce or limit localized intestinal distension around a portion of the intestine at a third location. In an additional embodiment, the device touches at least one of the second device and the third device. In yet an additional embodiment, the second device overlaps at least a portion of the device, and wherein the third device overlaps at least a portion of the second device. In another embodiment, the device, the second device, and the third device do not touch one another.

In an exemplary method of patient treatment of the present disclosure, the device comprises a temperature-sensitive material. In an additional embodiment, the device changes from a first configuration to a second configuration after introducing the device into the patient and prior to the step of positioning the device. In yet an additional embodiment, the first configuration is compressed, and wherein the second configuration is uncompressed. In another embodiment, the introducing step is performed by introducing at least part of a delivery device into the patient, wherein at least a portion of the device is positioned within the delivery device.

In an exemplary method of patient treatment of the present disclosure, the introducing step further comprises the step of removing the device from the delivery device. In another embodiment, the device is in a first, compressed configuration when at least a portion of the device is positioned within the delivery device, and wherein the device is in a second, uncompressed configuration after the device is removed from the delivery device. In yet another embodiment, the step of securing is performed by placing the one or more sutures within one or more suture apertures defined within the device. In an additional embodiment, the device comprises a flexible or pliable material.

In an exemplary device of the present disclosure, the device comprises a body configured for placement around a portion of an intestine of a patient and further configured to reduce or limit localized intestinal distension. In another embodiment, the device comprises a temperature-sensitive material so that the device can change from a first configuration to a second configuration after placement of the device within the patient. In yet another embodiment, one or more suture apertures are defined within the body. In an additional embodiment, the device is configured to transform from a compressed, first configuration during device delivery into the patient using a delivery device to an uncompressed, second configuration when the device is within the patient and outside of the delivery device.

In an exemplary device of the present disclosure, when the device is positioned around the intestine, the device facilitates weight loss of the patient. In an additional embodiment, the weight loss of the patient is facilitated by the reduction or limitation of localized intestinal distension, which slows overall digestive and/or excretory processes of the patient. In yet an additional embodiment, the weight loss of the patient is facilitated by the patient eating less food due to a slowing of overall digestive and/or excretory processes of the patient. In another embodiment, when the device is positioned around the intestine, the device treats a diabetic or other blood glucose level condition of the patient.

In an exemplary device of the present disclosure, the body comprises a flexible or pliable material. In another embodiment, the body comprises a biologically compatible polymer material. In yet another embodiment, the body further comprises a biologically compatible metal material. In an additional embodiment, the body comprises a biologically compatible metal material. In yet an additional embodiment, the body has a first, open configuration that can transform to a second, closed or partially closed configuration.

In an exemplary device of the present disclosure, the body defines a first end and a second end. In an additional embodiment, engagement of the first end and the second end effectively closes the device. In yet an additional embodiment, the body is configured for placement around at least half of a perimeter of the intestine. In another embodiment, the body is configured for placement around at least three quarters of a perimeter of the intestine. In yet another embodiment, the body is configured for placement completely around the intestine.

In an exemplary device of the present disclosure, the device has an inner diameter and an outer diameter when in a closed or partially closed configuration. In another embodiment, the device further comprises a hinged arm coupled to the body at a hinge location. In yet another embodiment, wherein when a hinged arm end engages a relative body end, the device is in a closed configuration. In an additional embodiment, the device further comprises a post and a post aperture defined within the body, the post configured to engage the post aperture to close the device. In yet an additional embodiment, the post is located at or near a first end of the body, and the post aperture is located at or near a second end of the body.

In an exemplary device of the present disclosure, a plurality of suture apertures are defined within the body. In an additional embodiment, when a suture is positioned within suture apertures located at relative opposing ends of the body, the device is in a closed configuration. In yet an additional embodiment, the plurality of suture apertures allows a user of the device to adjust an overall closed configuration size of the device.

In an exemplary device of the present disclosure, the device further comprises one or more tabs positioned at or near a first end of the body, and a tab receiver positioned at or near a second end of the body, the tab receiver configured to receive the one or more tabs to close the device. In another embodiment, the one or more tabs allow a user of the device to adjust an overall closed configuration size of the device. In yet another embodiment, the device further comprises a second body configured for placement around a portion of the intestine of the patient and further configured to reduce or limit localized intestinal distension.

In an exemplary system of the present disclosure, the system comprises a first intestinal device, comprising a body configured for placement around a portion of an intestine of a patient and further configured to reduce or limit localized intestinal distension, and a delivery device configured to receive at least a portion of the first intestinal device therein and further configured for at least partial placement into the patient to deliver the first intestinal device into the patient. In another embodiment, the system further comprises a second intestinal device, comprising a second body configured for placement around a portion of the intestine of the patient and further configured to reduce or limit localized intestinal distension. In yet another embodiment, the delivery device is further configured to receive at least a portion of the second intestinal device therein and to deliver the second intestinal device into the patient.

In an exemplary system of the present disclosure, the system comprises a first intestinal device and a second intestinal device, each comprising a body configured for placement around a portion of an intestine of a patient and further configured to reduce or limit localized intestinal distension. In another embodiment, the system further comprises a delivery device configured to receive at least a portion of the first intestinal device and the second intestinal device therein and further configured for at least partial placement into the patient to deliver the first intestinal device and the second intestinal device into the patient.

In an exemplary method of the present disclosure, the step of positioning the device is performed to position the device around the portion of the intestine selected from the group consisting of a duodenum, a jejunum, an ilium, and a large intestine. In another embodiment, the step of positioning the device is performed to position the device around a portion of a duodenum, and wherein the one or more sutures are attached to a stomach at or near a pyloric region. In yet another embodiment, when the device is positioned around the portion of the intestine, the device does not constrict the intestine. In an additional embodiment, when the device is positioned around the portion of the intestine, the intestine, when expanded due to digesting content therein, exerts a pressure against the device.

In an exemplary device of the present disclosure, the body is sized and shaped so not to invoke any stenosis of the intestine when placed around a portion of the intestine. In an additional embodiment, the body is sized and shaped so when the device is positioned around the portion of the intestine, the device does not constrict the intestine. In yet an additional embodiment, the body, when in the second, closed or partially closed configuration, defines an inner diameter that corresponds to an outer diameter of the intestine. In another embodiment, the body, when in the second, closed or partially closed configuration, defines an inner diameter that is larger than an outer diameter of the intestine.

BRIEF DESCRIPTION OF THE DRAWINGS

The disclosed embodiments and other features, advantages, and disclosures contained herein, and the matter of attaining them, will become apparent and the present disclosure will be better understood by reference to the following description of various exemplary embodiments of the present disclosure taken in conjunction with the accompanying drawings, wherein:

FIGS. 1A and 1B show a device of the present disclosure in an open or partially closed configuration, according to an exemplary embodiment of the present disclosure;

FIGS. 1C and 1D show a device of the present disclosure in a fully closed configuration, according to an exemplary embodiment of the present disclosure;

FIGS. 1E and 1F show a device of the present disclosure having a hinged portion, according to an exemplary embodiment of the present disclosure;

FIG. 1G shows a device of the present disclosure having a post and defining a post aperture, according to an exemplary embodiment of the present disclosure;

FIG. 1H shows a device of the present disclosure having a series of apertures defined therein in an open configuration, according to an exemplary embodiment of the present disclosure;

FIG. 1I shows a device of the present disclosure having a series of apertures defined therein in a closed configuration, according to an exemplary embodiment of the present disclosure;

FIG. 1J shows a device of the present disclosure having a plurality of tabs and a tab receiver, according to an exemplary embodiment of the present disclosure;

FIG. 1K shows a device of the present disclosure positioned around at least part of an intestine, according to an exemplary embodiment of the present disclosure;

FIGS. 3A and 3B show data indicative of an increase in injection volume during pressurization of duodenum and colon, respectively, according to the present disclosure;

FIGS. 3C and 3D show data indicative of an increase in diameter during pressurization of duodenum and colon, respectively, according to the present disclosure;

FIGS. 3E and 3F show data indicative of an increase in compensation volume rate during pressurization of duodenum and colon, respectively, according to the present disclosure;

FIGS. 5A and 5B show data indicative of the contractility of duodenum and colon vs. pressure relationship, respectively, according to the present disclosure;

FIGS. 5C and 5D show data indicative of the contractile tension of duodenum and colon vs. diameter relationship, respectively, according to the present disclosure;

FIGS. 6A-6D show data indicative of the relationship of duodenal and colonic contractility (amplitude) and incremental stretch ratio during pressurization, according to the present disclosure;

Figure 2:
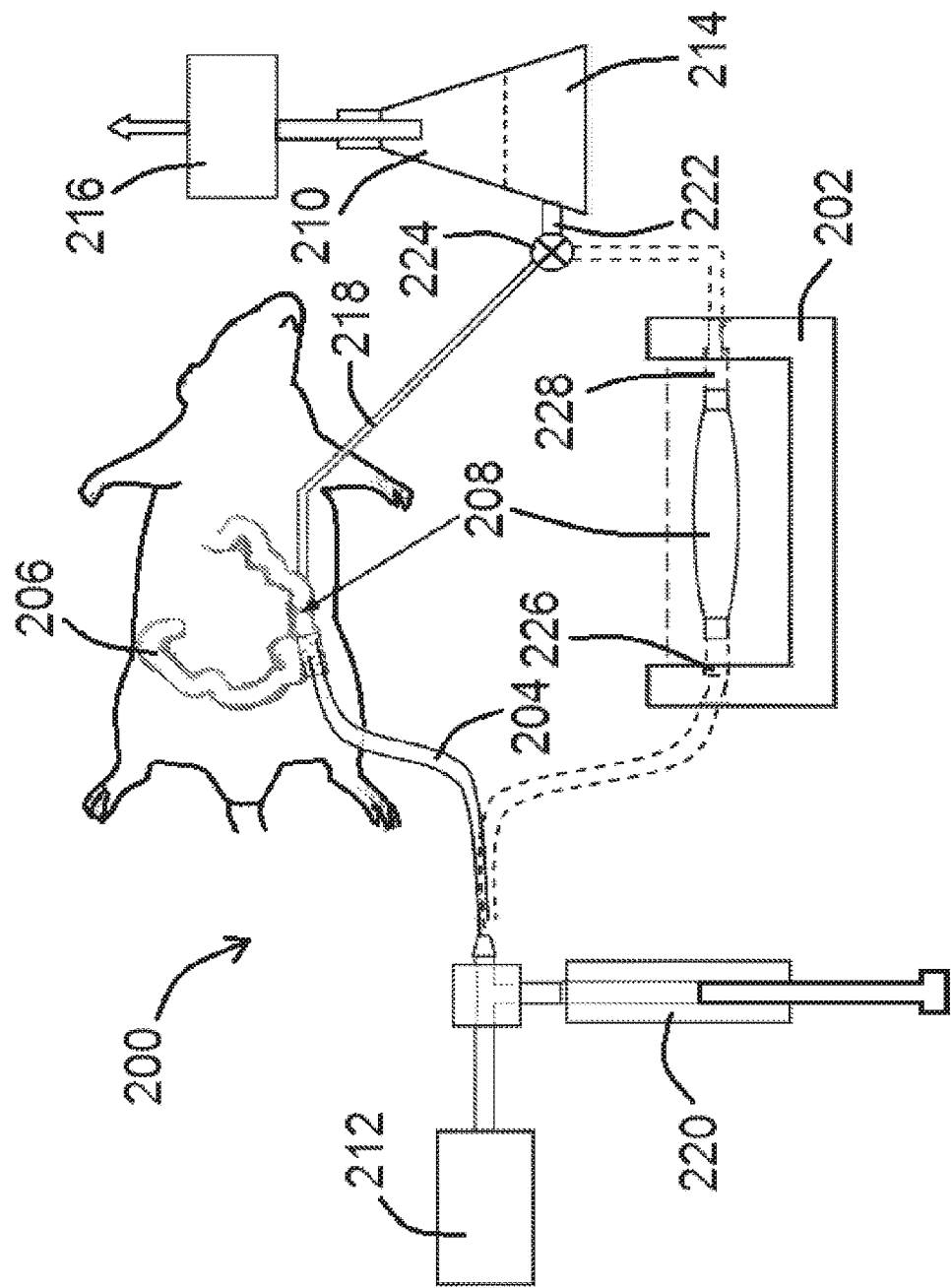
FIG. 2 shows an exemplary myograph used to test an exemplary intestinal device, according to at least one embodiment of the present disclosure.

An overview of the features, functions and/or configurations of the components depicted in the various figures will now be presented. It should be appreciated that not all of the features of the components of the figures are necessarily described. Some of these non-discussed features, such as various couplers, etc., as well as discussed features are inherent from the figures themselves. Other non-discussed features may be inherent in component geometry and/or configuration.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

An exemplary device for placement around a portion of an intestine to facilitate weight loss, to facilitate a reduction in food intake, to treat obesity, to treat a diabetic condition, to facilitate satiety, and/or to slow the overall digestive and/or excretory processes of a patient using the device of the present disclosure is shown in FIGS. 1A and 1B. As shown in FIGS. 1A and 1B, an exemplary device 100 comprises a body 102 configured for placement around a portion of (at least part of) an intestine 208, as shown in FIG. 1K, for example. The overall dimensions of an exemplary device 100 of the present disclosure are such to reduce/limit a localized intestinal expansion within a mammalian body where device 100 is positioned.

Device 100, in at least one embodiment, comprises a flexible/pliable material (such as any number of biologically compatible polymers and/or metals) that, when configured as a device 100 of the present disclosure, can fit around part of an intestine 208 and limit intestinal distension. As shown in FIGS. 1A and 1B, device 100 is in an open configuration, and as shown in FIGS. 1C and 1D, device 100 is in a fully closed configuration. Other embodiments of devices 100 of the present disclosure may have a partially closed configuration resembling to configurations shown in FIGS. 1A and 1B. However, and in various embodiments of devices 100 of the present disclosure, devices 100 may remain in an open configuration, and may never form a fully closed configuration, when positioned around at least part of an intestine 208, such as around most or a majority of a perimeter of an intestine 208. A device first end 104 and a device second end 106, as shown in FIGS. 1A and 1B, may engage one another upon closure of device 100, as shown in FIGS. 1C and 1D, or may be in close proximity to one another when device 100 is positioned around an intestine 208. One or more suture apertures 108, as shown in FIGS. 1A and 1C, may be defined within body 102 so that when device 100 is positioned around an intestine 208, sutures 144 (shown in FIG. 1I, such as silk sutures) may be used to secure device 100 around the intestine 208 to prevent device migration. In lieu of suture apertures 108, for example, one or more sutures 144 could be used and placed directly through and/or around portions of device 100.

An exemplary device 100 of the present disclosure has a length 110 (as shown in FIG. 1C) and an inner diameter 112 and an outer diameter 114 (as shown in FIG. 1D) when positioned around at least a portion of an intestine 208. In an open configuration, as shown in FIGS. 1A and 1B, the inner diameter 112 and outer diameter 114 (assuming a full circle) would be relatively larger than the inner diameter 112 and the outer diameter 114 of the same device in a closed or partially closed configuration. Other embodiments, as referenced in detail herein, may not have a relative inner diameter 112 or outer diameter 114 when not positioned around an intestine 208, but would have said diameters when positioned around at least a portion of an intestine 208. In addition, and as shown in FIG. 1D, device 100 has at least one inherent thickness 116, which may vary from embodiment to embodiment. Various device 100 embodiments can be configured as bands, sleeves, or cuffs, for example.

An additional embodiment of a device 100 of the present disclosure is shown in FIGS. 1E and 1F. As shown therein, device 100 comprises a hinged arm 118 connecting to part of body 102 at a hinge location 120. Hinged arm 118 is shown as being relatively open in FIGS. 1E and 1F, and would, in at least one embodiment, fully close so that a hinged arm end 122 would contact second end 106 of body 102. In other embodiments (not shown), hinged arm 118 would close but the entirety of device 100 may not actually close (such that first end 104 does not contact and/or overlap second end 106).

Additional device embodiments are shown in FIGS. 1G-1J. As shown in FIG. 1G, an exemplary device 100 may comprise a post 140 and define one or more post apertures 142, wherein when post 140 is positioned within post aperture 142, device 100 is secured in a closed configuration, around an intestine 208 if desired. In at least one embodiment, post 140 is at or near a first end 104 of the device, and post aperture 142 is located at or near a second end 106 of the device 100. FIGS. 1H and 1I show device 100 embodiments where two apertures 108 defined therein may be used to secure the device together using one or more sutures 144 as shown in FIG. 1I. FIG. 1H shows an exemplary device 100 in an open configuration, while FIG. 1I shows the same device 100 in a closed configuration with a suture 144 positioned through one or more suture apertures 108. Such an embodiment, having a plurality of apertures 108 defined therein, would allow a user positioning such a device 100 to be able to adjust the overall inner diameter 112 of the device 100 when positioning the same around an intestine 208.

An additional embodiment of a device 100 of the present disclosure is shown in FIG. 1J, whereby device 100 comprises one or more tabs 146 configured to fit within an aperture 147 of tab receiver 148, so that when a tab 146 is positioned within aperture 147 of tab receiver 148, tab receiver 148 holds that part of device 100 in place by way of tab 146. In at least one embodiment, the tabs 146 are at or near a first end 104 of the device, and the tab receiver 148 is located at or near a second end 106 of the device 100. Such an embodiment, having a plurality of tabs 146, would allow a user positioning such a device 100 to be able to adjust the overall inner diameter 112 of the device 100 when positioning the same around an intestine 208.

FIG. 1K shows an exemplary device 100 of the present disclosure positioned around at least part of an intestine 208. As shown therein, device 100 may be secured in place using one or more sutures 144 through apertures 108 and through part of a wall of intestine 208 to prevent device 100 migration. Removal of an exemplary device 100, in various embodiments, may be by way of removing sutures 144, disengaging post 140 from post aperture 142, removing tab 146 from tab receiver 148, etc., or by generally opening the device from a fully closed or partially closed configuration to a relatively open configuration. As noted in further detail below and shown in FIG. 7, two or more devices 100 can be placed in parallel (adjacent to one another (with or without spaces in between) or at least partially overlapping one another) to cover a larger portion of an intestine 208.

Figure 7:
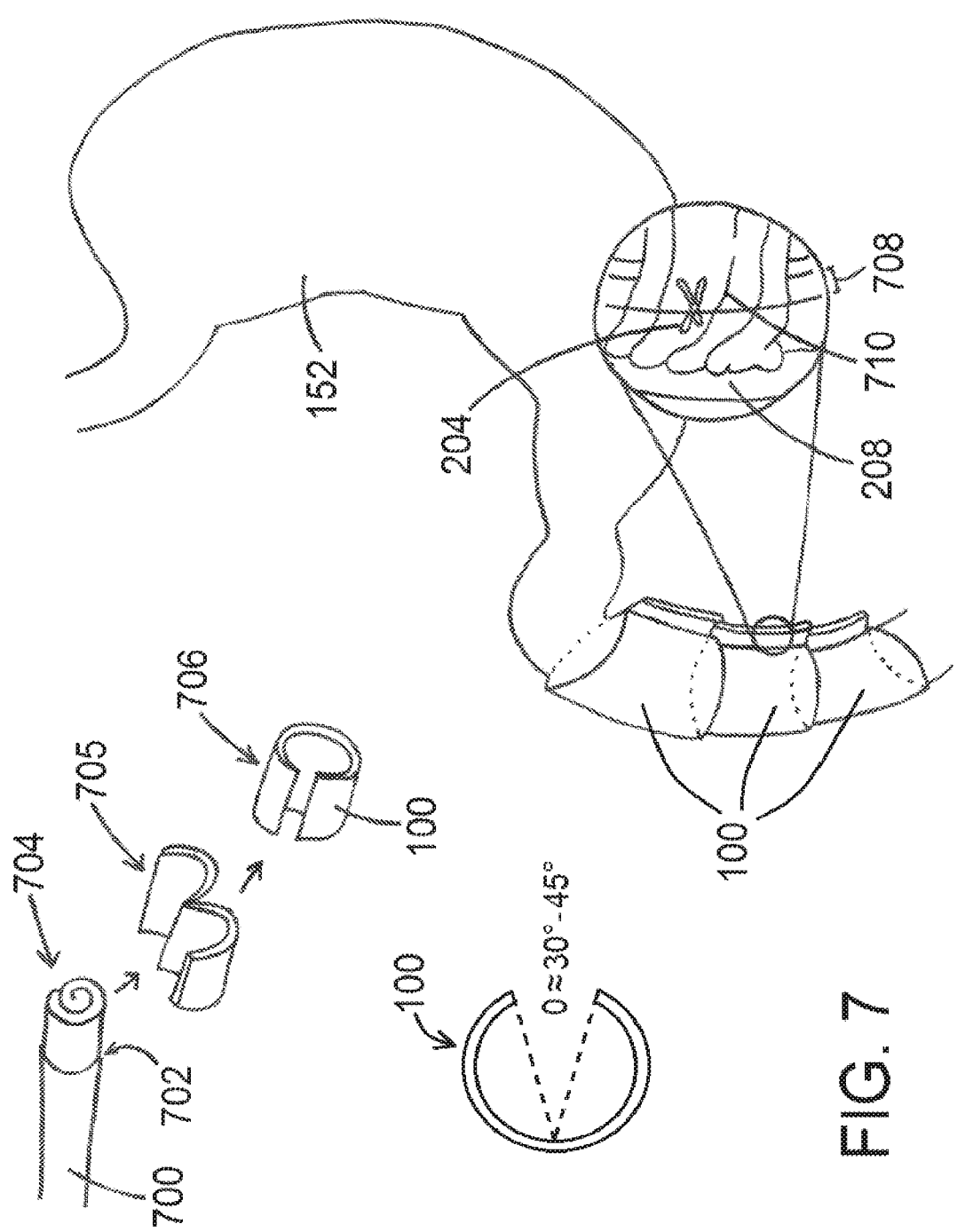
FIG. 7 shows use of a device around an intestine, according to an exemplary embodiment of the present disclosure.

Placement of various device 100 embodiments of the present disclosure around an intestine 208 may occur at various intestinal locations. The human small intestine, for example, extends from the pyloric region of the stomach and forms, from proximal end to the distal end, the duodenum, the jejunum, and the ilium, the latter of which is immediately adjacent to the proximal end of the large intestine. In at least one method of using a device 100 of the present disclosure, and as discussed in further detail herein, device 100 can be placed around the duodenum. FIG. 10C shows a portion of a mammalian digestive system 150, including the stomach 152, the pyloric region 154 of the stomach 152, and various intestine 208 portions, including the duodenum 156, the jejunum 158, the ilium 160, as well as the large intestine 162. As shown therein, an exemplary device 100 of the present disclosure is positioned around at least a portion of intestine 208, namely at duodenum 156, and is secured to stomach 152 at or near pyloric region 154 using one or more sutures 144. Placement of various device 100 embodiments may be made at one or more of the other above-referenced portions of intestine 208. As shown in FIG. 7, for example, three devices 100 can be used and positioned relative to one another at the duodenum 156.

Various device 100 embodiments of the present disclosure, which may also be referred to as non-constrictive cuffs (NCCs), may be made of polytetrafluoroethylene (PTFE), silicone rubber, or a bioabsorbable permeable or non-permeable material, for example. Such materials, and other biologically-compatible materials, would be sufficiently hard as to bear the forces generated from duodenal motility and distension but flexible enough to be configured to wrap around the duodenum 156 so that device 100 would be generally cylindrical.

FIG. 7 shows an exemplary embodiment of a device 100 of the present disclosure being delivered and positioned about an intestine 208. As shown in FIG. 7, an exemplary delivery device 700, which may be a general catheter, a delivery catheter, trocar, another type of tube, or a component having a lumen 702 defined therein, can be delivered laparoscopically, for example, into the patient so that a device 100 positioned therein can ultimately be delivered into the patient. In various embodiments, device 100 can have a first configuration 704, such as a folded, curled, or other configuration that is intended to facilitate delivery, and can have a second configuration 706, also as shown in FIG. 7, that is suitable for positioned about an intestine 208. First configuration 704, in various device 100 embodiments, may be the relatively open configuration, and second configuration 706 may be the partially or fully closed configuration. As shown in FIG. 7, an exemplary device 100 of the present disclosure has a relatively curled first configuration 704 that can open to an intermediate configuration 705 at a first temperature, and can ultimately change to a second configuration 706 at or near a second temperature. In at least one embodiment, the first temperature would be at or near room temperature (less than body temperature), and the second temperature would be at or near body temperature. To facilitate the change in configuration, temperature-sensitive materials such as nitinol can be used to comprise at least part of device 100, and devices 100 can be generally configured to have a first configuration 704 and a second configuration 706 suitable for delivery and placement, respectively. Materials comprising device 100, in such an embodiment, give device 100 a "memory" characteristic, such as changing from a first configuration 704 to a second configuration 706, whereby the second configuration 706 is a natural configuration at or near body temperature based upon the memory characteristic. Aside from temperature-sensitive materials, other materials that would allow device 100 to have a memory characteristic, such as a native partially or fully closed configuration, but also pliable/flexible enough to open, fold, or curl, for example, to facilitate delivery, may be used as well.

In various embodiments, the cross-section of device 100, such as shown in FIGS. 1B, 1D, and 7, may be generally circular or elliptical to fit the duodenal contour, whereby the longitudinal configuration of device 100 mimics the duodenal axial contour. In various embodiments, the inner diameter 114 of device 100, as shown in FIG. 1D, may be 105% to 150% of the duodenal external diameter. Furthermore, and in various embodiments, the length 110 of device 100, as shown in FIG. 1C, may vary from 10% to 80% of the entire length of duodenum 156, or may be even smaller (less than 10%), as shown in the general ring embodiment shown in FIG. 1C.

As shown in FIG. 7, and in various embodiments of devices 100 of the present disclosure, device 100 can be first collapsed (in a first configuration 704) to fit through standard trocar (an exemplary delivery device 100), and once in the abdomen, device 100 can be opened to sector for implantation and then folded back for wrapping the duodenum 156. When implanted, and in at least one embodiment of a method of using a device 100 of the present disclosure, device 100 will be first opened to sector and slipped half underneath the duodenum 156 from non-mesenteric side and then folded to wrap the duodenum 156. An axial gap 708 (0.6 to 2 mm, for example), in at least some device 100 embodiments, is made on device 100 to prevent disturbances to the mesentery 710 circulation of the bowel. Gap 708, also referred to as a lateral opening, on device 100 allows mesentery 710 access the duodenum 156 without compression to prevent ischemia. In at least some embodiments, and as shown in FIG. 7, an angle (θ) of our about 30° to 45° can be formed within device 100 to create gap 708, noting that smaller or larger gaps 708 may be used as well.

One or more sutures 144, such as shown in FIGS. 1K and 7 and as referenced above, may be used to secure an end of the device 100 (such as a proximal end) or another portion of device 100 on the stomach 152 at or near the pyloric sphincter to prevent device 100 migration. Additional sutures 144 may be made be placed axially along device 100 at the two edges of the sector with care to not close the sector to further reinforce the stiffness of device 100 during distension. Sutures 144, when placed as such, will penetrate the mesentery and stabilize device 100 in place during motility.

As shown in FIG. 7, more than one device 100 can be positioned about/upon intestine 208, either immediately adjacent to each other, with gaps in between, or overlapping one another. Based on the dimensions of intestine 208 at a particular location, said multiple devices 100 can be of different sizes (having different lengths 110 and/or diameters 112). Regarding device 100 sizes, preferred embodiments of the present disclosure are sized and shaped so not to invoke any intestine 208 stenosis. For example, and in various device 100 embodiments of the present disclosure, when devices 100 are in a fully or partially closed configuration around part or all of an intestine 208, device 100 does not constrict intestine 208, as the dimensions of device 100 exceed the native dimensions (perimeter, diameter, circumference, etc.) of intestine 208. For example, if a portion of a small intestine (such as duodenum 156) has an outer diameter of 5.0 cm, and it is desired to position an exemplary device 100 at that portion of duodenum 156, the dimensions of device 100 would be such that when device 100 is positioned around some or all of duodenum 156 at that portion/location, the effective inner diameter 112 of device 100 is greater than 5.0 cm. Devices 100 of the present disclosure, also referred to as non-constrictive cuffs as referenced above, are configured to avoid constricting intestine 208, but are configured, as noted above, to provide a restriction of intestine 208 beyond the normal non-distended intestinal dimensions. Accordingly, and in various device 100 embodiments of the present disclosure, inner diameter 112 of device 100, when in a partially or fully closed configuration, is greater than an outer diameter of intestine 208 at the location of placement of device 100 thereon. In at least various other device 100 embodiments, inner diameter 112 of device 100, when in a partially or fully closed configuration, is no less than the outer diameter of intestine 208 at the location of placement of device 100 thereon.

Various devices 100 of the present disclosure may be used to facilitate weight loss, or for other purposes as referenced herein, as follows. In at least one embodiment of a method of using such a device 100, the method comprises the step of delivering a device 100 laparoscopically (for example) into a patient relative to the patient's intestine 208. The device 100 may then be positioned around a patient's intestine 208 and secured in place using one or more closure mechanisms described herein and one or more sutures 144 if desired. Additional devices 100 may be delivered in a similar fashion if desired. In at least one embodiment of a method of the present disclosure, the device 100 may be delivered through an open surgical procedure. The device 100 may then be left in place for a desired amount of time, and ultimately removed by reversing the procedure (entering the patient, removing the device 100, and withdrawing the device 100 from the patient).

As described in detail below, use of such a device 100 can significantly attenuate the intestinal contractility in response to an increase in intraluminal pressure. Such a decrease in contractility has the effect of slowing the movement of food through a patient's gut during the digestion and excretion processes. Such a slowing of said processes, by way of contractility attenuation using a device of the present disclosure, would cause a patient to ultimately ingest less food, and therefore lose weight while the device 100 is positioned at least partially around the patient's intestine 208.

An exemplary device 100 of the present disclosure was tested using mouse intestine with an exemplary myograph as shown in FIG. 2 and referenced in further detail below. Other myograph embodiments, such as those disclosed within U.S. Patent Application Publication No. 2010/0022265 of Kassab and Lu, may also be used to perform the tests described below.

FIG. 2 shows an exemplary system (myograph) 200, such as the myograph used in the present study, and the in situ/in vitro experimental setup, used in the present study. As shown in FIG. 2, system 200 comprises a chamber 202 with a catheter 204 on one side wall of the chamber 202 which bridges the lumen 206 of an intestine 208 to an inflation flask 210 and pressure transducer 212. A 50 ml inflation flask 210 with PSS 214 (connected to a pressure regulator 216) inflated the intestine 208 to the desired pressure. The catheter 204, a solid state pressure transducer 212 (SPR-524, Microtip catherter transducer, Millar Inc, Texas), a tube 218 to the inflation flask 210, and a compensatory microsyringe 220 were assembled using a connector 222. The clamping of tube 218 between inflation flask 210 and intestine 208, by way of clamp 224, achieved isovolumic conditions, i.e., the intestinal lumen volume was constant.

The compensatory microsyringe 220 (50 µl gastight microsyringe, UltraMicroPump III, and Micro 4™ microsyringe controll, World Precision Instruments, USA) was used to stablize (maintain) the baseline pressure since water transport across the intestinal wall changes the intraluminal pressure. The criteria for compensation was to maintain the contour of periodic pressure at baseline. The rate of compensation generally changed with inflation pressure. A CCD camera on a microscope and an image proccessing system tracked the intestinal diameter. As the intestine was inflated to a desired pressure (e.g., 5 mmHg, 10 mmHg, etc.), the clamp 224 was closed, and the intestinal contraction or relaxation was quantified by the variation of intraluminal pressure under a constant rate of compensation. The isovolumic system 200 recorded the periodic contractions of intestine in response to changes of inflation pressure. The isovolumic measurements usually lasted 5 to 10 minutes and the intestine 208 was reversed to proximal and distal open as in physiological state.

The animal experiments were performed as follows. Twelve C57BL/6J mice at 24 weeks of age, having 31.2±5.8 grams of body weight, were obtained from Jackson Laboratory. The animals were acclimated to the facility for approximately one (1) week prior to the start of the study. The animals were anesthetized with xylazine (1 mg/kg, i.p.) and ketamine (9 mg/kg, i.p.) and maintained with xylazine (0.5 mg/kg) and ketamine (4.5 mg/kg) every half hour. The animal experiments were performed in accordance with the guidelines of Institute of Laboratory Animal Research Guide, Public Health Service Policy, Animal Welfare Act, and an approved IACUC protocol.

In situ intestinal contractility. Under anesthesia, the abdominal skin and muscle layers of the animal were opened to expose either the duodenum or the distal colon. The intestine was moistened with warm (37° C.) HEPES physiological saline solution (HEPES-PSS in mmole/L: 119 NaCl, 4.7 KCl, 3 HEPES acid, 2.3 HEPES sodium salt, 1.17 $MgSO_4$, 1.6 CaCl, 5.5 Dextrose). The applied PSS was aerated with 95% $O_2$ and 5% $CO_2$. The intestine was cannulated with a HEPES-PSS prefilled catheter (ID: 1 mm, OD: 2 mm) which connected to the isovolumic system 200 as shown in FIG. 2. A 2 mm incision was cut at the oral intestine where the catheter 204 (having an outer diameter of 2 mm) was inserted into the intestinal lumen. The incision was tied on the catheter 204 with 6-0 silk suture twice to ensure no leakage. Two milliliters of PSS was gently injected into the intestine through the catheter 204 to wash away the content. Another 6-0 silk suture was tied 11 mm away towards the anal intestine from the cannulation. The intestinal mesentery was untouched to allow the intestine to work in a physiological environment maintaining normal circulation and vagal responses.

In vitro intestinal contractility. The animals were euthanized by overanesthesia. Deudenum or distal colon was excised quickly and placed in ice cold (4° C.) PSS to slow down cellular metabolism and preserve cell vitality during preparation. The adjacent tissue was dissected with the aid of a stereo microscope. The intestine was allowed to warm up to room temperature (22° C.) slowly over approximately 10-15 minutes and was transferred to a chamber 202 of the isovolumic myograph 200 with HEPES-PSS (22° C.). The two ends of the intestine were cannulated to connectors 226, 228 (having an inner diameter of 1 mm and an outer diameter of 2 mm) in the chamber 202 of the isovolumic myograph 200 and the length of the intestine considered was 11 mm. The content in the intestine was gently rinsed with HEPES-PSS. The intestine in the chamber 202 was slowly warmed to 37° C. over approximately 15-20 minutes and equilibrated for 30 minutes at a basal pressure of about 1 mmHg before distension.

Intestinal contractility and inflation pressure. The mechanical stimulation of intestine was induced by random sequence of intraluminal inflation pressures. The intestinal contraction was quantified by the intraluminal pressure under isovolumic condition and the contractility was characterized with the amplitude and period of the pressure waveforms. The intestine was inflated to a desired pressure by a pressure regulator 216 connected to flask 210 as referenced above. The clamping of the tube 222 between the inflation flask 210 and the intestine 208 maintained a constant volume of solution in the intestinal lumen (an isovolumic condition). The compensatory microsyringe 220 maintains isovolumic conditions at, for example, an infusion rate of 0.6-2.3 µl/min. The data was discarded if the rate was larger than 5 µl/min since this implied damage (leakage) of the intestinal wall. At isovolumic conditions, the variations of intraluminal pressure were recorded with a data acquisition system (Biopac, MP100, Houston, Tex.). The amplitude, frequency, and contractile duration of pressure waveforms were analyzed to characterize the intestinal contractility.

Intestinal restraint: A loosely fitting restraint (an exemplary device 100 of the present disclosure) made of plastic tube (body 102) was used to determine the role of stretch. A portion of body 102 was removed (semi-cylinder) to allow the intestinal mesentery to pass through freely. The dimensions of body 102 used in the study were 12.5 mm in length, 6 mm in internal diameter, and 2 mm in wall thickness, noting that bodies 102 of different dimensions may also be used in similar studies. The width of the semi-cylinder was about 0.3 mm. The semi-cylinder was axially opened up to a sector with the aid of a forceps. The semi-cylinder was passed through the intestine. The forceps was released to allow the semi-cylinder to fully wrap the intestine. The semi-cylinder was circumferentially tied with a 6-0 silk suture to restrain the intestine into the lumen of the semi-cylinder when the intesine was inflated. Device 100 covered the cylindrical area and limited the stretch of intestinal circumference despite an increase in intraluminal pressure in the intestine. The noncovered intestinal wall on the two ends was distended during the increase in intraluminal pressure. To verify that the duodenal nerves were not damaged while mounting the restraint, the contractility was measured again after removal of device 100.

Protocol of mechanical stimulation. The intraluminal pressure was increased stepwise to 2, 5, 10, 15, 20, 30, 40, and 50 (colon only) mmHg by injection of HEPES PSS into the intestine at rate of 0.05 ml/min, respectively. The intestinal contraction at isovolumic condition was recorded by the changes of pressure at each inflation or distension pressure. This protocol was applied to both in situ and in vitro intestine with or without intestinal restraint. In the experiment of in vitro intestine, acetylcholine ($10^{-6}$ mole/l) was used to elicit non-neuroactive contraction of intestinal smooth muscle at intraluminal pressure of 40 mmHg (duodenum) or 50 mmHg (colon) to evalute contractility of intestinal smooth muscle.

Data Analysis and Statistics. The intestinal contractile amplitude was represented by the amplitude of pressure variation. The incremental stretch ratios of intestinal circumference during the stepwise inflation were computed with and without device 100. The contractile tension was calculated by the amplitude of pressure multiplied by the intestinal diameter. The linear regression of intestinal contractility and incremental stretch was then analyzed. The data were presented as mean ±SD and significant differences between groups were determined by student t-test. Significant differences between the in situ, in vitro, and restraint groups were determined by use of Analysis Of Variance (ANOVA) between groups. A probability of $p<0.05$ was considered indicative of a statistically significant difference.

Results. The injection volumes into duodenum and colon for both in situ and in vitro inflation were summarized in FIGS. 3A and 3B, respectively, which increased rapidly during low pressure and slowed down during high pressure. Changes of injection volume, diameter, and compensation rate during pressurization of duodenum (left column) and colon (right column) are generally shown in FIGS. 3A-3F. FIGS. 3A and 3B show an increase in injection volume during pressurization of duodenum and colon, respectively. Inflation volume was significantly smaller when restraint applied. FIGS. 3C and 3D show an increase in diameter during pressurization of duodenum and colon, respectively. Diameter did not change when restraint was applied. FIGS. 3E and 3F show an increase in compensation volume rate during pressurization of duodenum and colon, respectively. Compensation rate was suppressed by restraint. There were no difference between in situ and in vitro states ($p>0.05$), and the restraint significantly reduced the injection volume, diameters, and compensation rate at in situ and in vitro states ($p<0.05$). As shown within the figures, ◊ indicated an in situ state, ♦ indicates an in situ state with a restraint, Δ indicates an in vitro state, and ▲ indicates an in vitro state with a restraint.

As shown in the figures, the diameters had a similar trend to the injection volume (FIGS. 3C and 3D), which reflect the circumferential distensibility of the duodenum and colon during pressurization. The compensatory rates of duodenum and colon at isovolumic condition increased rapidly during low pressure and slowed down during high pressure (FIGS. 3E and 3F, respectively). The compensatory rates, diameters, and compensatory rates were not significantly different between in situ and in vitro inflation ($p>0.05$). The application of the restraint (an exemplary device 100 of the present disclosure) on the duodenum or colon limited the increase of in situ and in vitro injection volume, diameters, and compensatory rates during pressurization, as shown in FIGS. 3A-3F.

Figure 4B:
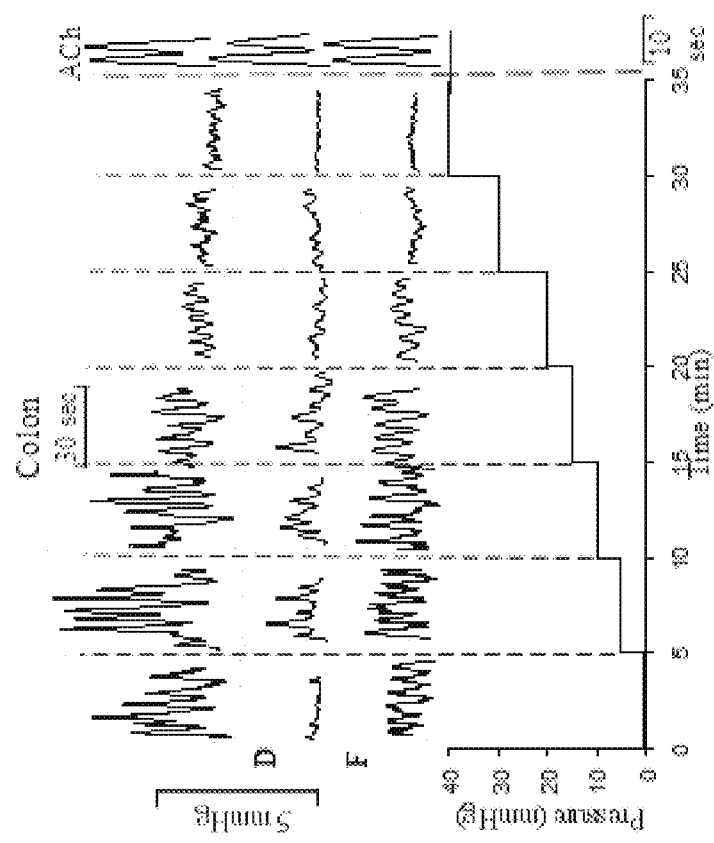
FIGS. 4A and 4B show data indicative of temporal contractile waves of the duodenum and colon, according to the present disclosure.
Figure 4A:
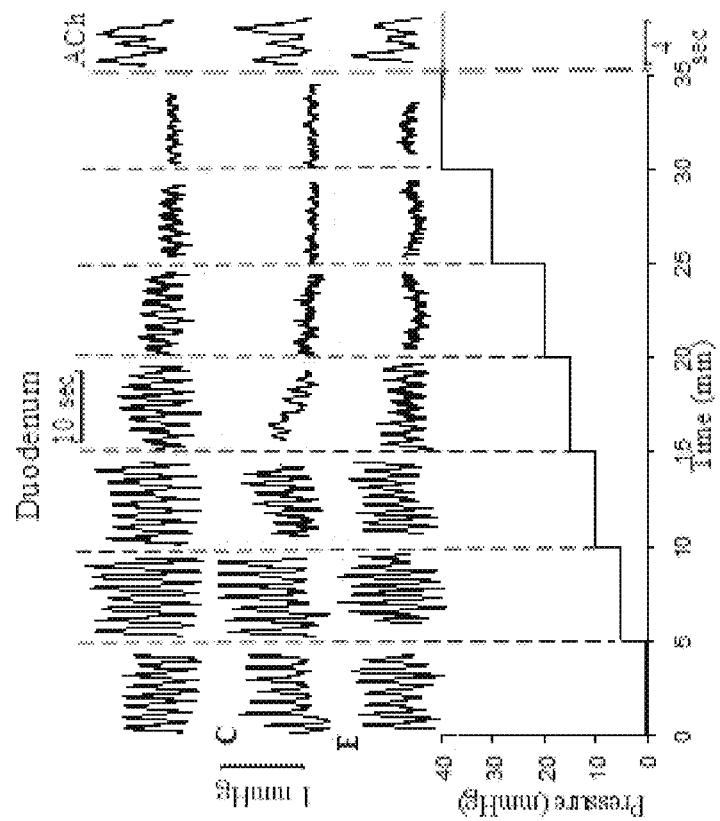

The typical intraluminal pressure waveforms produced by contraction of duodenum and colon are shown in FIGS. 4A-4F in which the amplitude of intraluminal pressure was affected by changes in inflation pressure. FIGS. 4A-4F generally show typical in situ and in vitro temporal contractile pressure waves of duodenum (left column) and colon (right column) at various inflation pressures. As shown in FIGS. 4A and 4B, and without restraint, the in situ contractile pressure waves of duodenum and colon were significant. As shown in FIGS. 4C and 4D, also without restraint, the in vitro contractile pressure waves of duodenum and colon were significantly attenuated in comparison with in situ state. When a restraint was applied, as shown in FIGS. 4E and 4F, the in situ contractile pressure waves of duodenum and colon were significantly attenuated. The amplitude reached a maximum under all conditions at 5 mmHg of inflation pressure and decreased monotonically with further increase of inflation pressure. The in vitro contraction of colon was significantly attenuated as shown in FIG. 4D.

As generally shown in FIGS. 5A-5D, the contractility of duodenum (left column) and colon (right column) as a function of pressure or diameter. FIGS. 5A and 5B show the contractility of duodenum and colon vs. pressure relationship, respectively, whereby the restraint significantly reduced the contractility of duodenum and colon at in situ and in vitro states ($p<0.05$). FIGS. 5C and 5D show the contractile tension of duodenum and colon vs. diameter relationship, respectively, whereby the restraint significantly reduced the contractile tension of duodenum and colon at in situ and in vitro states ($p<0.05$). As shown within the figures, ◊ indicated an in situ state, ♦ indicates an in situ state with a restraint, Δ indicates an in vitro state, and ▲ indicates an in vitro state with a restraint.

The contractility of duodenum and colon are shown as a function of inflation pressure in FIGS. 5A and 5B, respectively. The in situ contractility of duodenum increased from 0.97±0.29 to 1.42±0.39 mmHg when the inflation pressure was increased from 1 to 5 mmHg. The duodenal contractility then decreased significantly down to 0.4±0.28 mmHg when the inflation pressure was further increased from 5 to 40 mmHg as shown in FIG. 5A. The in situ contractility of colon increased from 4.15±1.16 to 4.86±1.32 mmHg when the inflation pressure increased from 1 to 5 mmHg. The colonic contractility, then, decreased significantly down to 1.61±0.98 mmHg when the inflation pressure was further increased from 5 to 50 mmHg as shown in FIG. 5B. The restraint did not affect the in situ duodenal contractility at lower inflation pressures (<5 mmHg), but attenuated the contractility when the inflation pressures were >10 mmHg as shown in FIG. 5A. However, the restraint largely attenuated the in situ colonic contractility in the entire range of inflation pressures as shown in FIG. 5B. The in vitro contractility of duodenum linearly decreased with increase in inflation pressure and was significantly attenuated in comparison with the in situ contractility as shown in FIG. 5A. The in vitro contractility of colon was significantly attenuated in comparison with the in situ contractility as shown in FIG. 5B. The presence of the restraint essentially abolished the in vitro contractility of duodenum and colon in the entire range of inflation pressures (shown in FIGS. 5A and 5B, respectively).

The in vitro smooth muscle contraction of duodenum and colon stimulated by ACh, however, was still similar to maximum contractility at the in situ state. The contractility of duodenum and colon recovered 95-100% when the restraint was removed, which confirms that the application of in situ restraint did not damage the nerve fibers or vasculature of duodenum and colon. The relationship between contractile tension and diameter of duodenum and colon were analyzed in FIGS. 5C and 5D, respectively. There was significant peak of contractile tension in both in situ and in vitro preparations, which implicates duodenal and colonic smooth muscle appears similar to skeletal and cardiac muscle which generates the maximal tension at an optimal length. The restraint was smaller than the optimal length and hence significantly attenuated the contraction of duodenum and colon.

FIGS. 6A-6D generally show the relationship of duodenal and colonic contractility (amplitude) and incremental stretch ratio during pressurization. FIG. 6A is indicative of the duodenum inflated without restraint, and in FIG. 6B, the duodenum was restrained while inflated. Linear regression showed an excellent linear relationship in FIG. 6A but not in 6B. FIG. 6C is indicative of the colon inflated without restraint, and in FIG. 6D, the colon was restrained while inflated. Linear regression showed an excellent linear relationship in FIG. 6C but not in 6D. A linear regression of intestinal contractility and incremental strain suggests a direct correlation of circumferentially incremental strain and contractility (shown in FIGS. 6A and 6B) of in vitro and in situ duodenum and colon (shown in Table 1, below, wherein $R^2 > 0.9$).

TABLE 1

The slope, intercept, and $R^2$ of linear regression by least-squares fit

| | Slope | Intercept | $R^2$ | P value |
|---|---|---|---|---|
| Duodenum: | | | | |
| In vivo | 4.62 ± 1.03 | 0.42 ± 0.11 | 0.933 ± 0.311 | 0.047-0.012 |
| Ex vivo | 4.55 ± 1.16 | 0.14 ± 0.08 | 0.985 ± 0.32* | 0.041-0.009 |
| In vivo restraint | 3.12 ± 1.36 | 0.41 ± 0.29† | 0.523 ± 0.28 | 0.095-0.053 |
| Ex vivo restraint | 2.72 ± 1.31 | 0.23 ± 0.21‡ | 0.376 ± 0.22 | 0.169-0.073 |
| Colon: | | | | |
| In vivo | 11.0 ± 2.08 | 1.31 ± 0.29 | 0.953 ± 0.33 | 0.043-0.011 |
| Ex vivo | 6.80 ± 1.71 | 0.89 ± 0.15* | 0.916 ± 0.32* | 0.049-0.019 |
| In vivo restraint | 8.16 ± 2.96 | 1.39 ± 0.73† | 0.697 ± 0.25 | 0.093-0.049 |

TABLE 1-continued

The slope, intercept, and $R^2$ of linear regression by least-squares fit

| | Slope | Intercept | $R^2$ | P value |
|---|---|---|---|---|
| Ex vivo restraint | 4.73 ± 2.64 | 0.41 ± 0.39‡ | 0.579 ± 0.21‡ | 0.096-0.049 |

Notes:
*$P < 0.05$ indicates statistical difference between "ex vivo" and "in vivo".
†$P < 0.05$ indicates statistical difference between "in vivo restraint" and "in vivo".
‡$P < 0.05$ indicates statistical difference between "ex vivo restraint" and "ex vivo".

The intercept of linear regression, which reflects the offset of the contractility response to stretch stimulation, significantly shifted downward in in vitro duodenum and colon as shown in Table 1. The slope, which reflects the amplification of the contractility response to stretch stimulation, significantly decreased in in vitro colon but did not change among in situ duodenum. With the restraint (an exemplary device 100), the $R^2$ of linear regression decreased significantly in both in vitro and in situ intestines and became statistically non-significant. FIGS. 6C and 6D show that the intestinal contractility response to incremental strain is blunted by the circumferential restraint. The slopes decreased due to the restraint in both in situ and in vitro duodenum and colon, and the intercept decreased due to the restraint in in vitro colon, as shown in Table 1.

As referenced herein, an isovolumic myograph (system 200) was used to assess the role of pressure-induced distension (stretch or strain and tension) on intestinal contractility for both in situ and in vitro preparations and an external restraint was used to separate the effect of distension from pressure. The studies revealed that the intestine remained normally contractile when stretch was induced by intraluminal pressures <10 mmHg. When stretch was induced by the intraluminal pressure of >10 mmHg, intestinal contractility weakened. There was a different pattern of contractility from duodenum to colon in response to stretch stimulation. Furthermore, a linear correlation was found between intestinal contractility and incremental strain which implicates the role of stretch in intestinal contractility.

The isovolumic myograph may be a useful method to evaluate the intestinal global contractility for understanding the effect of stimulations of intraluminal pressure on intestinal contraction. The advantages of isovolumic myograph to wire and pressure myographs include the utility to make in situ measurements and application of an external restraint (an exemplary device 100 of the present disclosure). The restraint blocks the distension induced by intraluminal pressure and hence separates the effect of distension from pressure. In fact, the application of a restraint in this study limited the increase of diameter during inflation as shown in FIGS. 3C and 3D. The restraint attenuated the in situ and in vitro intestinal contractility induced by inflation pressure (shown in FIGS. 5A and 5B), which is consistent with the prior studies on the pressure-induced contraction of ileum. This result implicates the role of stretch in intestinal contractility.

Further analysis shows that incremental strain plays a stimulatory role in both in situ and in vitro states through a dose-response relation, as shown in FIGS. 6A and 6B. The restraint attenuates incremental strain and weakened the duodenal and colonic contractility, as shown in FIGS. 6C and 6D. Both the slope and intercept were changed by the restraint as demonstrated in Table 1 for in situ/in vitro states and with/without restraint.

Additional studies were performed in connection with the present disclosure to determine the effect in body weight by using an exemplary device 100 of the present disclosure. A peri-intestinal cuff (exemplary device 100) was externally implanted on the proximal duodenum to achieve body weight loss and metabolic restoration. Device 100 was implanted peri-intestinally at 107% larger than the external diameter of duodenum in order not to provide a physical obstruction on the duodenum (so that device 100 was non-constrictive), positioned adjacent to the pyloric sphincter. As noted above, placement of device 100 about the intestine 208 decreases the motility of intestine 208. Device 100 reduces the contractility when chyme pass through and therefore increases the transit time of the chime, whereby an increased transit time would relate to weight loss and satiety.

Furthermore, use of devices 100 of the present disclosure affects epithelial function on the duodenum covered under device 100 and hence affects absorption of nutrients not only at the site of device 100 but beyond since remodeling (wall thickening) is observed to extend beyond the site of placement. Intimal thickening occurs with minimal medial smooth muscle cell damage under an uninterrupted endothelial cell layer when one or more devices 100 are placed. The increased thickness may also cause nutritional and glucose absorption changes.

Figure 8A:
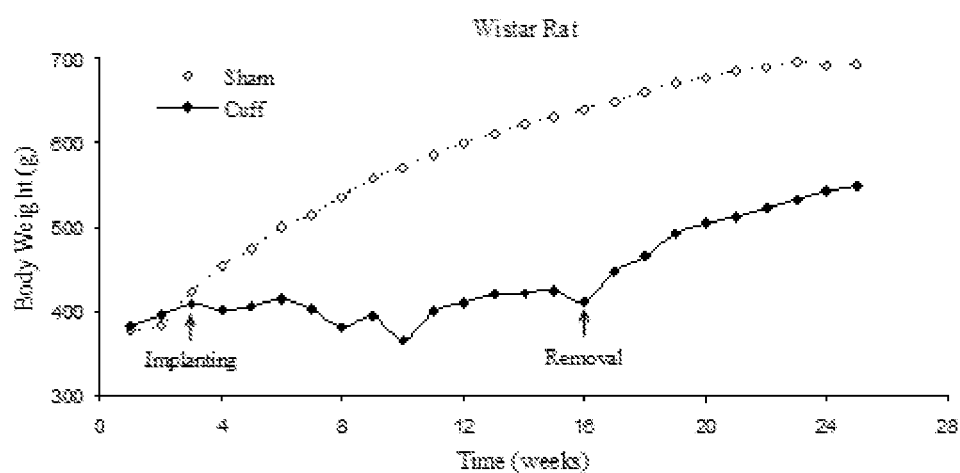
FIGS. 8A-8C show data indicative of weight loss, food intake, and glucose levels, respectively, with and without use of a device in Wistar rats, according to the present disclosure.
Figure 8B:
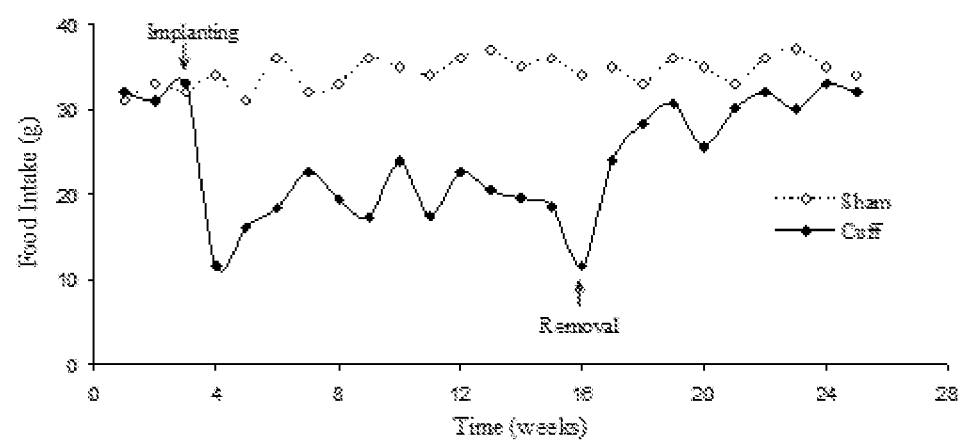
Figure 8C:
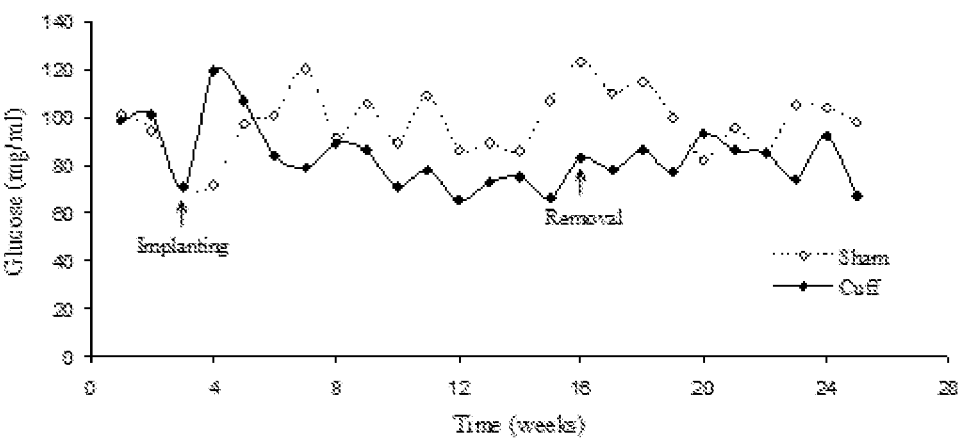
Figure 9A:
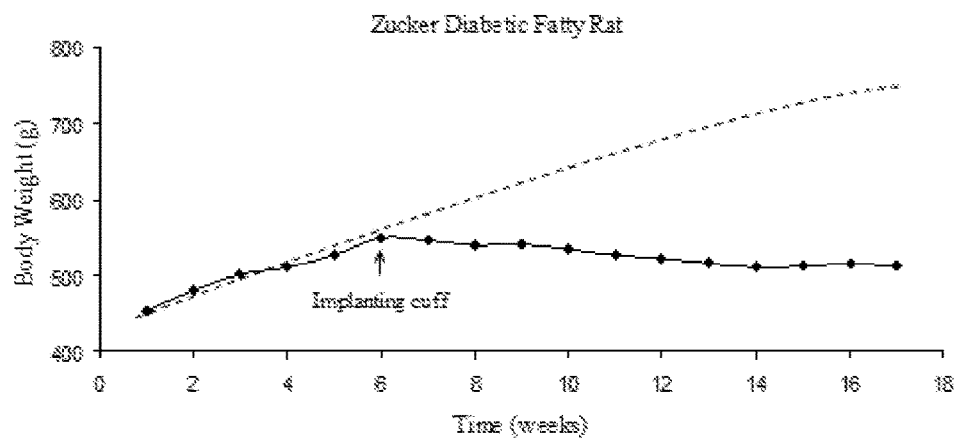
FIGS. 9A-9C show data indicative of weight loss, food intake, and glucose levels, respectively, with and without use of a device in Zucker diabetic fatty rats, according to the present disclosure.
Figure 9B:
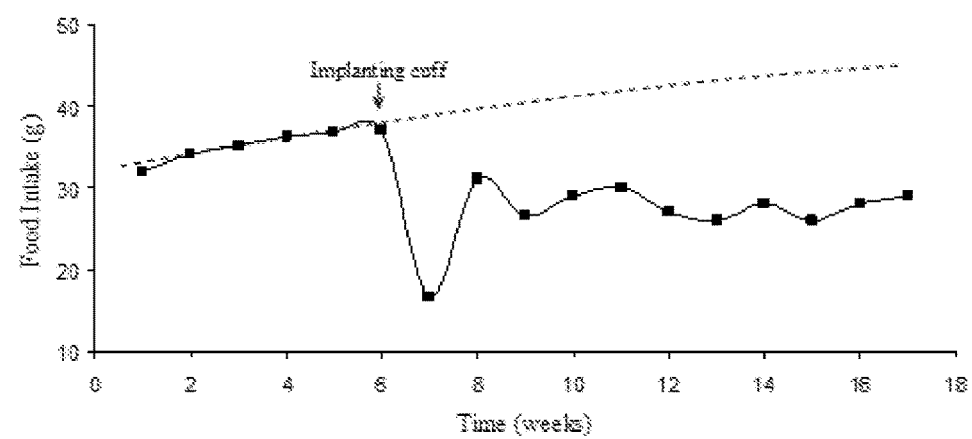
Figure 9C:
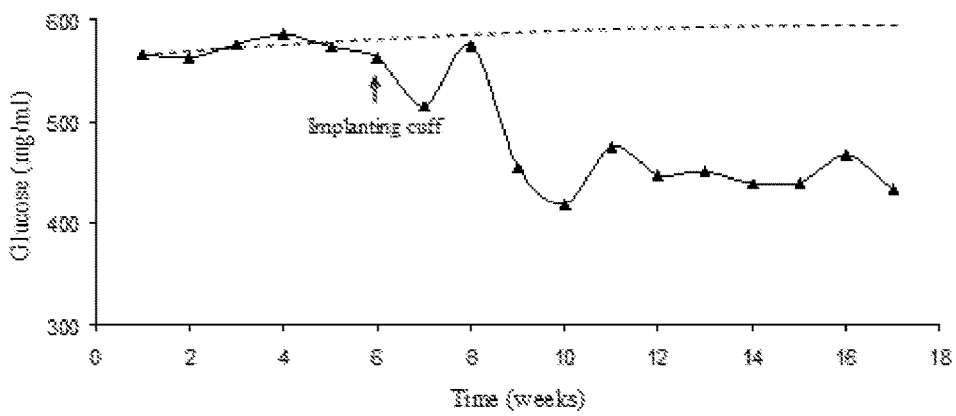

FIGS. 8A-9C show food intake, weight loss and blood glucose concentration for normal (Wistar, FIGS. 8A-8C) and diabetic (Zucker diabetic fatty, FIGS. 9A-9C) rats, respectively. Said figures show a cause and effect relation between use of device 100 and food intake/weight loss where placement cause the decreases and removal cause reversal of the effect. As shown in FIGS. 8A-8C, cuff (device 100) implantation reduced body weight and food intake in Wistar rats, and body weight and food intake were recovered after removal of device 100. FIGS. 9A-9C show reductions in weight, food intake, and plasma glucose levels in Zucker diabetes fatty rats. Accordingly, use of exemplary devices 100 of the present disclosure can cause patients to lose weight, decrease food intake/ingestion, and/or reduce blood glucose levels, the latter being indicative of a treatment for diabetes or another bodily condition impacted by levels of blood glucose.

Figure 10A:
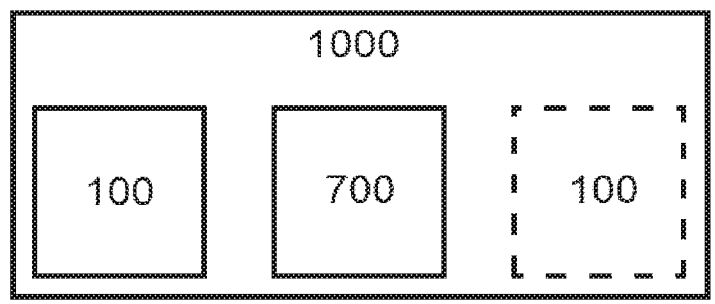
FIGS. 10A and 10B show block diagrams of systems, according to exemplary embodiments of the present disclosure.
Figure 10B:
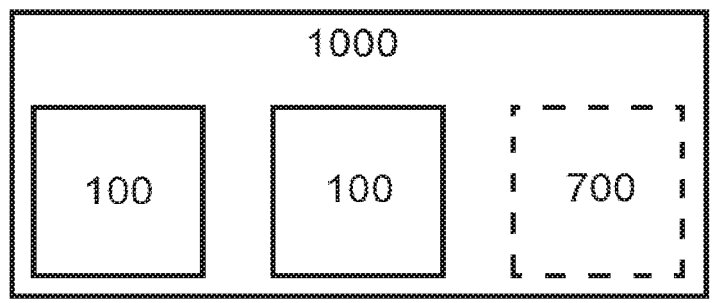
Figure 10C:
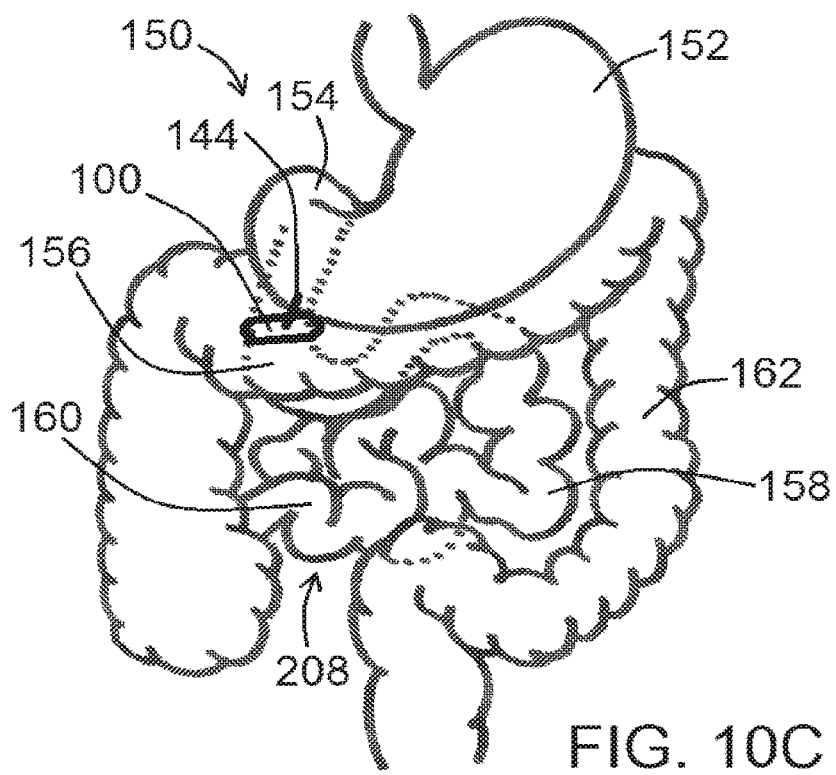
FIG. 10C shows use of a device around a duodenum, according to an exemplary embodiment of the present disclosure.

FIGS. 10A and 10B show block diagrams of components of exemplary systems of the present disclosure. As shown in FIG. 10A for example, an exemplary system 1000 (having one or more purposes referenced herein, such as to facilitate weight loss, to facilitate a reduction in food intake, to treat a blood glucose level condition, etc.) may comprise one or more devices 100 of the present disclosure and an exemplary delivery device 700 of the present disclosure. A second device 100 is shown as optional in FIG. 10A. Such a system 1000 may have one, two, or more devices 100. FIG. 10B shows a block diagram of components of another exemplary system 1000 of the present disclosure, comprising at least two devices 100 and an optional delivery device 700. Additional components of the present disclosure may also comprise one or more exemplary systems 1000 of the present disclosure.

In general, and as referenced herein, devices 100 and/or systems 1000 can be considered as solutions to various patient problems, such as obesity and diabetes. If a patient is attempting to lose weight, but for whatever reasons cannot, various devices 100 and/or systems 1000 of the present disclosure can solve the patient's problem of not losing weight or problem of being overweight. Similarly, should a patient have a problem with overeating, have a general excess weight problem not rising to the level of obesity, have a blood glucose problem not rising to the level of diabetes, etc., one or more of those problems could be solved using various devices 100 and/or systems 1000 of the present disclosure.

Pressure-induced distension has been confirmed as a stimulator of intestinal afferent sensors. The afferent nerve is excited significantly in response to inflation, which initiates the sensory transmission to central nervous system. Intestinal mechanosensors are located in the intestinal wall, and the increase of pressure in lumen causes contraction of longitudinal muscle of intestine and elicits a peristaltic reflex of intestine where nervous activation is involved. The myogenic response of intestinal smooth muscle and efferent neurogenic contraction are regulated by mechanosensors and enteric nerves. The relation between efferent vagus signals and intestinal distension was identified decades ago. The mechanosensors in intestinal wall are primary sensors of mechanical stimulation. In the study referenced herein, the application of an external restraint terminated the pressure-induced distension and attenuated the intestinal contractility, which suggests that stretch or tension but not inflation pressure is the stimulus for intestinal mechanosensors.

The efferent (motor) vagus signals are responses of central nervous system to the afferent (sensory) vagus stimulation. Intestinal contractility is regulated by the extrinsic nervous system (parasympathetic and sympathetic nervous systems) and the intrinsic nervous system. One of the physiological functions of efferent signals is to regulate the intestinal contractility. Here, in situ and in vitro preparations provided the evidence of nervous regulation. The in vitro preparation implicates the efferent-independent (local regulatory) contraction, in which the efferent nervous signals are interrupted and appear to impact mechanically distension-induced contractility.

Intestinal contractility disorders can arise from intestinal obstruction or ileus. Laparotomy and manipulation also interfere with intestinal movements. The most widely accepted explanation of postoperative ileus is based on the premise that intestinal manipulation inhibits motor function through some neurologic reflex response. Experimental studies have identified central neural influences that mediate ileus of the gastrointestinal tract. An interesting observation is that the efferent vagus (motor) inactivation may occur after abdominal surgery, e.g., postoperative intestinal ileus. The intestinal ileus (obstruction) may be mediated by central neural influences, neurologic reflex (sensitive afferent nerves) response, the disturbances of myoelectrical activity, humoral responses, and local or regional activation of immune system function. The contractility pattern in response to diameter or pressure as referenced herein may mirror the physical mechanism where surgery or inflammation slows motility of intestine.

The present approach has some limitations that warrant discussion. The isovolumic condition is non-physiological since it blocks the fluid (or content) movement in intestine from oral to anal portions and may affect peristaltic reflex of intestine. An isovolumic myograph only provides the global but not the local contraction of isolated intestine. To understand the interaction of intestinal nervous activation and smooth muscle contraction, isovolumic myography must be combined with measurements of nervous activation (nervous firing spikes) in additional studies. The external restraint may result in ischemia or affect the lymphatic system, albeit it was confirmed that the restraint was reversible (i.e., function was restored after removal).

The isovolumic myograph 200 may be a component used in a powerful method to evaluate the intestinal global contractility suitable for understanding the effect of stimulations of intraluminal pressure and on intestinal contraction. The regional contraction cannot be measured with this method and additional approaches are needed to assess local contraction. An isovolumic condition also blocks the fluid (or content) movement in intestine from oral to anal portions, which may affect peristaltic reflex of intestine. Since this is a non-physiological condition, isovolumic conditions were maintained intermittingly and then restored the physiological state. The advantage of isovolumic myograph to wire and pressure myographs is the utility to make in situ measurements While various embodiments of intestinal devices for facilitating weight loss and methods of using the same have been described in considerable detail herein, the embodiments are merely offered as non-limiting examples of the disclosure described herein. It will therefore be understood that various changes and modifications may be made, and equivalents may be substituted for elements thereof, without departing from the scope of the present disclosure. The present disclosure is not intended to be exhaustive or limiting with respect to the content thereof.

Further, in describing representative embodiments, the present disclosure may have presented a method and/or a process as a particular sequence of steps. However, to the extent that the method or process does not rely on the particular order of steps set forth therein, the method or process should not be limited to the particular sequence of steps described, as other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

The invention claimed is:

1. A device, comprising:
a first intestinal device and a second intestinal device, each defining a longitudinal axis along its length and each comprising:
a body configured for placement around a portion of an intestine of a patient and further configured to reduce or limit localized intestinal distension and to facilitate weight loss of the patient; and
wherein when deployed, the first intestinal device is longitudinally adjacent the second intestinal device and a proximal end of the first intestinal device longitudinally overlaps a distal end of the second device.

2. The device of claim 1, wherein the device comprises a temperature-sensitive material so that the device can change from a first configuration to a second configuration after placement of the device within the patient.

3. The device of claim 1, wherein the body defines an axial gap which defines a 30-45 degree arc of an outer circumference of the body when measured from an opposite side of the body.

4. The device of claim 1, wherein the device is configured to transform from a compressed, first configuration during device delivery into the patient using a delivery device to an uncompressed, second configuration when the device is within the patient and outside of the delivery device.

5. The device of claim 1, wherein when the device is positioned around the intestine, the device treats a diabetic or other blood glucose level condition of the patient.

6. The device of claim 1, wherein the body comprises a flexible or pliable material.

7. The device of claim 1, wherein the body comprises a biologically compatible material.

8. The device of claim 1, wherein the body has a first, open configuration that can transform to a second, closed or partially closed configuration.

9. The device of claim 1, wherein the body defines a first end and a second end, and wherein engagement of the first end and the second end effectively closes the device.

10. The device of claim 1, wherein the body is configured for placement around at least half of a perimeter of the intestine.

11. The device of claim 1, wherein the body is configured for placement completely around the intestine.

12. The device of claim 1, wherein the body is sized and shaped so not to invoke any stenosis of the intestine when placed around a portion of the intestine.

13. The device of claim 1, wherein the body is sized and shaped so when the device is positioned around the portion of the intestine, the device does not constrict the intestine.

14. The device of claim 1, further comprising:
a hinged arm coupled to the body at a hinge location;
wherein when a hinged arm end engages a relative body end, the device is in a closed configuration; and
wherein the device is in an open position when the hinged arm extends radially outward.

15. The device of claim 1, further comprising:
a post and a post aperture defined within the body, the post configured to engage the post aperture to close the device.

16. The device of claim 1, further comprising:
one or more tabs positioned at or near a first end of the body; and
a tab receiver positioned at or near a second end of the body, the tab receiver configured to receive the one or more tabs to close the device;
wherein the one or more tabs allows a user of the device to adjust an overall closed configuration size of the device.

17. A system, comprising:
a first intestinal device and a second intestinal device, each defining a longitudinal axis along its length and comprising a body configured for placement around a portion of an intestine of a patient and further configured to reduce or limit localized intestinal distension and to facilitate weight loss of the patient, wherein the first intestinal device is disposed longitudinally adjacent the second intestinal device and a proximal end of the first intestinal device longitudinally overlaps a distal end of the second device;
a delivery device defining a longitudinal axis along its length and configured to receive at least a portion of the first intestinal device therein and further configured for at least partial placement into the patient to deliver the first intestinal device into the patient; and
wherein the first intestinal device and the second intestinal device are is received in the delivery device such that the longitudinal axes of the first intestinal device and the second intestinal device and the longitudinal axis of the delivery device are aligned.

18. A system, comprising:
a first intestinal device and a second intestinal device, each defining a longitudinal axis along its length and comprising a body configured for placement around a portion of an intestine of a patient and further configured to reduce or limit localized intestinal distension, the system configured to facilitate weight loss of the patient;

wherein the first intestinal device and the second intestinal device both define an internal diameter; and the first intestinal device is disposed longitudinally adjacent the second intestinal device such that a proximal end of the first intestinal device at least partially longitudinally overlaps a distal end of the second intestinal device.

19. The system of claim 18, further comprising:

a delivery device configured to receive at least a portion of the first intestinal device and the second intestinal device therein and further configured for at least partial placement into the patient to deliver the first intestinal device and the second intestinal device into the patient.

20. The system of claim 18, wherein the first intestinal device and the second intestinal device further comprise a generally circular or elliptical cross section.

\* \* \* \* \*